United States Patent
Camps et al.

(10) Patent No.: US 11,339,420 B2
(45) Date of Patent: May 24, 2022

(54) **FLUORESCENCE-BASED REPORTERS FOR MUTAGENESIS DETECTION IN *E. COLI***

(71) Applicant: The Regents of the University of California, Oakland, CA (US)

(72) Inventors: Manel Camps, Santa Cruz, CA (US); Jennifer Allen, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 124 days.

(21) Appl. No.: 16/473,442

(22) PCT Filed: Dec. 26, 2017

(86) PCT No.: PCT/US2017/068410
§ 371 (c)(1),
(2) Date: Jun. 25, 2019

(87) PCT Pub. No.: WO2018/125863
PCT Pub. Date: Jul. 5, 2018

(65) Prior Publication Data
US 2019/0330676 A1    Oct. 31, 2019

Related U.S. Application Data

(60) Provisional application No. 62/441,411, filed on Jan. 1, 2017.

(51) Int. Cl.
*C12Q 1/34* (2006.01)
*C12N 9/86* (2006.01)
*C12N 1/20* (2006.01)
*C12N 15/70* (2006.01)
*C12N 15/72* (2006.01)

(52) U.S. Cl.
CPC ............... *C12Q 1/34* (2013.01); *C12N 9/86* (2013.01); *C12N 15/72* (2013.01); *C12Y 305/02006* (2013.01)

(58) Field of Classification Search
None
See application file for complete search history.

(56) References Cited

U.S. PATENT DOCUMENTS

| 2003/0092099 | A1  | 5/2003 | Clark |
| 2005/0070006 | A1* | 3/2005 | Reifferscheid ....... C12Q 1/6883 435/252.34 |
| 2011/0070594 | A1  | 3/2011 | Colpas et al. |
| 2012/0302461 | A1* | 11/2012 | Camps ............... G01N 33/5023 506/10 |

FOREIGN PATENT DOCUMENTS

EP    0444775    6/1996

OTHER PUBLICATIONS

Standley et al., "Fluorescence-Based Reporters for Detection of Mutagenesis in *E. coli*", Methods Enzymol. published online Jun. 9, 2017, 26 pages (Year: 2017).*
Suzuki et al., "Probing the mutation spectrum in *E. coli*", Nucleic Acids Symp Ser (Oxford) 2007:289-290 (Year: 2007).*
Schmid et al., "Mutagenicity test system based on a reporter gene assay for short-term detection of mutagens (MutaGen assay)", Mutat. Res. 535:55-72, 2003 (Year: 2003).*
PCT/US2017/068410, "International Search Report and Written Opinion", dated Apr. 24, 2018, 14 pages.
PCT/US2017/068410, "International Preliminary Report on Patentability", dated Jul. 11, 2019, 11 pages.

* cited by examiner

*Primary Examiner* — David Steadman
(74) *Attorney, Agent, or Firm* — Kilpatrick Townsend & Stockton LLP

(57) ABSTRACT

Direct detection of mutagenesis in prokaryotes by reversion of an inactivating mutation (reversion mutation assay), producing a quantitative signal for in vivo mutagenesis, may greatly reduce the amount of test chemicals and labor involved in these assays. Further, transcriptional coupling of β-lactamase reversion and GFP, translational fusion between β-lactamase and GFP with stop codon in GFP, and a novel dual reporter to monitor continuous mutagenesis may be used in methods described herein.

10 Claims, 10 Drawing Sheets

Specification includes a Sequence Listing.

WT Pol I  LF- Pol I

SEQUENCE LISTING

<160> NUMBER OF SEQ ID NOS: 46

<210> SEQ ID NO 1
<211> LENGTH: 861
<212> TYPE: DNA
<213> ORGANISM: Unknown
<220> FEATURE:
<223> OTHER INFORMATION: Multiple species; nucleotide sequence encoding
      wild-type TEM-1

<400> SEQUENCE: 1

```
atgagtattc aacatttccg tgtcgccctt attccctttt tgcggcatt ttgccttcct      60 gttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagcactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
```

| | |
|---|---|
| gatcgttggg aaccggagct gaatgaagcc ataccaaacg acgagcgtga caccacgatg | 540 |
| cctgtagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga dataggtgcc | 840 |
| tcactgatta agcattggta a | 861 |

<210> SEQ ID NO 2
<211> LENGTH: 861
<212> TYPE: DNA
<213> ORGANISM: Artificial Sequence
<220> FEATURE:
<223> OTHER INFORMATION: Synthetic construct

<400> SEQUENCE: 2

| | |
|---|---|
| atgagtattc aacatttccg tgtcgccctt attcccttt ttgcggcatt ttgccttcct | 60 |
| gtttttgctc acccagaaac gctggtgaaa gtaaaagatg ctgaagatca gttgggtgca | 120 |
| cgagtgggtt acatcgaact ggatctcaac agcggtaaga tccttgagag ttttcgcccc | 180 |
| gaagaacgtt ttccaatgat gccaactttt aaagttctgc tatgtggcgc ggtattatcc | 240 |
| cgtattgacg ccgggcaaga gcaactcggt cgccgcatac actattctca gaatgacttg | 300 |
| gttgagtact caccagtcac agaaaagcat cttacggatg gcatgacagt aagagaatta | 360 |
| tgcagtgctg ccataaccat gagtgataac actgcggcca acttacttct gacaacgatc | 420 |
| ggaggaccga aggagctaac cgcttttttg cacaacatgg ggatcatgt aactcgcctt | 480 |
| gatcgttggg aaccggagct gaatgaagcc ataccaaacg acgagcgtga caccacgatg | 540 |
| cctgtagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga gataggtgcc | 840 |
| tcactgatta agcattggta a | 861 |

<210> SEQ ID NO 3
<211> LENGTH: 861
<212> TYPE: DNA
<213> ORGANISM: Artificial Sequence
<220> FEATURE:
<223> OTHER INFORMATION: Synthetic construct

<400> SEQUENCE: 3

| | |
|---|---|
| atgagtattc aacatttccg tgtcgccctt attcccttt ttgcggcatt ttgccttcct | 60 |
| gtttttgctc acccagaaac gctggtgaaa gtaaaagatg ctgaagatca gttgggtgca | 120 |
| cgagtgggtt acatcgaact ggatctcaac agcggtaaga tccttgagag ttttcgcccc | 180 |
| gaagaacgtt ttccaatgat gacaactttt aaagttctgc tatgtggcgc ggtattatcc | 240 |
| cgtattgacg ccgggcaaga gcaactcggt cgccgcatac actattctca gaatgacttg | 300 |
| gttgagtact caccagtcac agaaaagcat cttacggatg gcatgacagt aagagaatta | 360 |
| tgcagtgctg ccataaccat gagtgataac actgcggcca acttacttct gacaacgatc | 420 |
| ggaggaccga aggagctaac cgcttttttg cacaacatgg ggatcatgt aactcgcctt | 480 |

```
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatgatgaa cgaaatagac agatcgctga gataggtgcc    840
tcactgatta agcattggta a                                              861
```

```
<210> SEQ ID NO 4
<211> LENGTH: 861
<212> TYPE: DNA
<213> ORGANISM: Artificial Sequence
<220> FEATURE:
<223> OTHER INFORMATION: Synthetic construct

<400> SEQUENCE: 4
atgagtattc aacatttccg tgtcgccctt attcccttt ttgcggcatt ttgccttcct     60 gttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gagaactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatgatgaa cgaaatagac agatcgctga gataggtgcc    840
tcactgatta agcattggta a                                              861
```

```
<210> SEQ ID NO 5
<211> LENGTH: 861
<212> TYPE: DNA
<213> ORGANISM: Artificial Sequence
<220> FEATURE:
<223> OTHER INFORMATION: Synthetic construct

<400> SEQUENCE: 5
atgagtattc aacatttccg tgtcgccctt attcccttt ttgcggcatt ttgccttcct     60 gttttgctc acccagaaac gctggtgaaa gtaaaagatg ctgaagatca gttgggtgca    120
cgagtgggtt acatcgaact ggatctcaac agcggtaaga tccttgagag ttttcgcccc    180
gaagaacgtt ttccaatgat gtgaactttt aaagttctgc tatgtggcgc ggtattatcc    240
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
```

```
ggaggaccga aggagctaac cgcttttttg cacaacatgg gggatcatgt aactcgcctt      480
gatcgttggg aaccggagct gaatgaagcc ataccaaacg acgagcgtga caccacgatg      540
cctgtagcaa tggcaacaac gttgcgcaaa ctattaactg gcgaactact tactctagct      600
tcccggcaac aattaataga ctggatggag gcggataaag ttgcaggacc acttctgcgc      660 tcggccttc cggctggctg gtttattgct gataaatctg gagccggtga gcgtgggtct       720
cgcggtatca ttgcagcact ggggccagat ggtaagccct cccgtatcgt agttatctac      780
acgacgggga gtcaggcaac tatggatgaa cgaaatagac agatcgctga gataggtgcc      840
tcactgatta agcattggta a                                                861

<210> SEQ ID NO 6
<211> LENGTH: 861
<212> TYPE: DNA
<213> ORGANISM: Artificial Sequence
<220> FEATURE:
<223> OTHER INFORMATION: Synthetic construct

<400> SEQUENCE: 6
atgagtattc aacatttccg tgtcgccctt attcccttt ttgcggcatt ttgccttcct        60 gttttgctc acccagaaac gctggtgaaa gtaaaagatg ctgaagatca gttgggtgca       120
cgagtgggtt acatcgaact ggatctcaac agcggtaaga tccttgagag ttttcgcccc      180
gaagaacgtt ttccaatgat gaacactttt aaagttctgc tatgtggcgc ggtattatcc     240
cgtattgacg ccgggcaaga gcaactcggt cgccgcatac actattctca gaatgacttg      300
gttgagtact caccagtcac agaaaagcat cttacggatg gcatgacagt aagagaatta     360
tgcagtgctg ccataaccat gagtgataac actgcggcca acttacttct gacaacgatc     420
ggaggaccga aggagctaac cgcttttttg cacaacatgg gggatcatgt aactcgcctt      480
gatcgttggg aaccggagct gaatgaagcc ataccaaacg acgagcgtga caccacgatg      540
cctgtagcaa tggcaacaac gttgcgcaaa ctattaactg gcgaactact tactctagct      600
tcccggcaac aattaataga ctggatggag gcggataaag ttgcaggacc acttctgcgc      660 tcggccttc cggctggctg gtttattgct gataaatctg gagccggtga gcgtgggtct       720
cgcggtatca ttgcagcact ggggccagat ggtaagccct cccgtatcgt agttatctac      780
acgacgggga gtcaggcaac tatggatgaa cgaaatagac agatcgctga gataggtgcc      840
tcactgatta agcattggta a                                                861

<210> SEQ ID NO 7
<211> LENGTH: 861
<212> TYPE: DNA
<213> ORGANISM: Artificial Sequence
<220> FEATURE:
<223> OTHER INFORMATION: Synthetic construct

<400> SEQUENCE: 7
atgagtattc aacatttccg tgtcgccctt attcccttt ttgcggcatt ttgccttcct        60 gttttgctc acccagaaac gctggtgaaa gtaaaagatg ctgaagatca gttgggtgca       120
cgagtgggtt acatcgaact ggatctcaac agcggtaaga tccttgagag ttttcgcccc      180
gaagaacgtt ttccaatgat gcgcactttt aaagttctgc tatgtggcgc ggtattatcc     240
cgtattgacg ccgggcaaga gcaactcggt cgccgcatac actattctca gaatgacttg      300
gttgagtact caccagtcac agaaaagcat cttacggatg gcatgacagt aagagaatta     360
tgcagtgctg ccataaccat gagtgataac actgcggcca acttacttct gacaacgatc     420
```

-continued

```
ggaggaccga aggagctaac cgcttttttg cacaacatgg gggatcatgt aactcgcctt      480
gatcgttggg aaccggagct gaatgaagcc ataccaaacg acgagcgtga ccaccacgat      540
cctgtagcaa tggcaacaac gttgcgcaaa ctattaactg gcgaactact tactctagct      600
tcccggcaac aattaataga ctggatggag gcggataaag ttgcaggacc acttctgcgc      660
tcggcccttc cggctggctg gtttattgct gataaatctg gagccggtga gcgtgggtct      720
cgcggtatca ttgcagcact ggggccagat ggtaagccct cccgtatcgt agttatctac      780
acgacgggga gtcaggcaac tatggatgaa cgaaatagac agatcgctga gataggtgcc      840
tcactgatta agcattggta a                                               861
```

<210> SEQ ID NO 8
<211> LENGTH: 286
<212> TYPE: PRT
<213> ORGANISM: Unknown
<220> FEATURE:
<223> OTHER INFORMATION: Mulitple species; protein sequence of wild-type TEM-1

<400> SEQUENCE: 8

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270
```

Arg Gln Ile Ala Glu Ile Gly Ala Ser Leu Ile Lys His Trp
                275                 280                 285

<210> SEQ ID NO 9
<211> LENGTH: 238
<212> TYPE: PRT
<213> ORGANISM: Artificial Sequence
<220> FEATURE:
<223> OTHER INFORMATION: Synthetic construct

<400> SEQUENCE: 9

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 10
<211> LENGTH: 238
<212> TYPE: PRT
<213> ORGANISM: Artificial Sequence
<220> FEATURE:
<223> OTHER INFORMATION: Synthetic construct

<400> SEQUENCE: 10

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

```
Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235
```

<210> SEQ ID NO 11
<211> LENGTH: 238
<212> TYPE: PRT
<213> ORGANISM: Artificial Sequence
<220> FEATURE:
<223> OTHER INFORMATION: Synthetic construct

<400> SEQUENCE: 11

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Arg Gln Asn Thr Pro Ile Gly Asp Gly Pro
            180                 185                 190
```

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 12
<211> LENGTH: 536
<212> TYPE: PRT
<213> ORGANISM: Artificial Sequence
<220> FEATURE:
<223> OTHER INFORMATION: Synthetic construct

<400> SEQUENCE: 12

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys Gly Ser
225                 230                 235                 240

Ala Gly Ser Ala Ala Gly Ser Gly Glu Phe Met Ser Ile Gln His Phe
                245                 250                 255

Arg Val Ala Leu Ile Pro Phe Phe Ala Ala Phe Cys Leu Pro Val Phe
            260                 265                 270

Ala His Pro Glu Thr Leu Val Lys Val Lys Asp Ala Glu Asp Gln Leu
        275                 280                 285

Gly Ala Arg Val Gly Tyr Ile Glu Leu Asp Leu Asn Ser Gly Lys Ile
290                 295                 300

Leu Glu Ser Phe Arg Pro Glu Glu Arg Phe Pro Met Met Ser Thr Phe
305                 310                 315                 320

Lys Val Leu Leu Cys Gly Ala Val Leu Ser Arg Ile Asp Ala Gly Gln
                325                 330                 335

Glu Gln Leu Gly Arg Arg Ile His Tyr Ser Gln Asn Asp Leu Val Glu
            340                 345                 350

Tyr Ser Pro Val Thr Glu Lys His Leu Thr Asp Gly Met Thr Val Arg
        355                 360                 365

Glu Leu Cys Ser Ala Ala Ile Thr Met Ser Asp Asn Thr Ala Ala Asn
    370                 375                 380

Leu Leu Leu Thr Thr Ile Gly Gly Pro Lys Glu Leu Thr Ala Phe Leu
385                 390                 395                 400

His Asn Met Gly Asp His Val Thr Arg Leu Asp Arg Trp Glu Pro Glu
                405                 410                 415

Leu Asn Glu Ala Ile Pro Asn Asp Glu Arg Asp Thr Thr Met Pro Val
            420                 425                 430

Ala Met Ala Thr Thr Leu Arg Lys Leu Leu Thr Gly Glu Leu Leu Thr
        435                 440                 445

Leu Ala Ser Arg Gln Gln Leu Ile Asp Trp Met Glu Ala Asp Lys Val
    450                 455                 460

Ala Gly Pro Leu Leu Arg Ser Ala Leu Pro Ala Gly Trp Phe Ile Ala
465                 470                 475                 480

Asp Lys Ser Gly Ala Gly Glu Arg Gly Ser Arg Gly Ile Ile Ala Ala
                485                 490                 495

Leu Gly Pro Asp Gly Lys Pro Ser Arg Ile Val Val Ile Tyr Thr Thr
            500                 505                 510

Gly Ser Gln Ala Thr Met Asp Glu Arg Asn Arg Gln Ile Ala Glu Ile
        515                 520                 525

Gly Ala Ser Leu Ile Lys His Trp
    530                 535

<210> SEQ ID NO 13
<211> LENGTH: 27
<212> TYPE: DNA
<213> ORGANISM: Artificial Sequence
<220> FEATURE:
<223> OTHER INFORMATION: Synthetic construct

<400> SEQUENCE: 13
tttccaatga tgccaacttt taaagtt        27

<210> SEQ ID NO 14
<211> LENGTH: 27
<212> TYPE: DNA
<213> ORGANISM: Artificial Sequence
<220> FEATURE:
<223> OTHER INFORMATION: Synthetic construct

<400> SEQUENCE: 14
actcacgtta agggattttg gtcatga        27

<210> SEQ ID NO 15
<211> LENGTH: 25
<212> TYPE: DNA
<213> ORGANISM: Artificial Sequence
<220> FEATURE:
<223> OTHER INFORMATION: Synthetic construct

<400> SEQUENCE: 15
ttccaatgat gacaactttt aaagt        25

<210> SEQ ID NO 16
<211> LENGTH: 27
<212> TYPE: DNA
<213> ORGANISM: Artificial Sequence
<220> FEATURE:
<223> OTHER INFORMATION: Synthetic construct

<400> SEQUENCE: 16
actcacgtta agggattttg gtcatga                                           27

<210> SEQ ID NO 17
<211> LENGTH: 21
<212> TYPE: DNA
<213> ORGANISM: Artificial Sequence
<220> FEATURE:
<223> OTHER INFORMATION: Synthetic construct

<400> SEQUENCE: 17
ccaatgatga gaacttttaa a                                                 21

<210> SEQ ID NO 18
<211> LENGTH: 27
<212> TYPE: DNA
<213> ORGANISM: Artificial Sequence
<220> FEATURE:
<223> OTHER INFORMATION: Synthetic construct

<400> SEQUENCE: 18
actcacgtta agggattttg gtcatga                                           27

<210> SEQ ID NO 19
<211> LENGTH: 25
<212> TYPE: DNA
<213> ORGANISM: Artificial Sequence
<220> FEATURE:
<223> OTHER INFORMATION: Synthetic construct

<400> SEQUENCE: 19
ttccaatgat gtgaactttt aaagt                                             25

<210> SEQ ID NO 20
<211> LENGTH: 27
<212> TYPE: DNA
<213> ORGANISM: Artificial Sequence
<220> FEATURE:
<223> OTHER INFORMATION: Synthetic construct

<400> SEQUENCE: 20
actcacgtta agggattttg gtcatga                                           27

<210> SEQ ID NO 21
<211> LENGTH: 21
<212> TYPE: DNA
<213> ORGANISM: Artificial Sequence
<220> FEATURE:
<223> OTHER INFORMATION: Synthetic construct

<400> SEQUENCE: 21
ccaatgatga acacttttaa a                                                 21

<210> SEQ ID NO 22
<211> LENGTH: 27
<212> TYPE: DNA
<213> ORGANISM: Artificial Sequence
<220> FEATURE:
<223> OTHER INFORMATION: Synthetic construct

<400> SEQUENCE: 22
actcacgtta agggattttg gtcatga                                              27

<210> SEQ ID NO 23
<211> LENGTH: 21
<212> TYPE: DNA
<213> ORGANISM: Artificial Sequence
<220> FEATURE:
<223> OTHER INFORMATION: Synthetic construct

<400> SEQUENCE: 23
ccaatgatgc gcacttttaa a                                                    21

<210> SEQ ID NO 24
<211> LENGTH: 27
<212> TYPE: DNA
<213> ORGANISM: Artificial Sequence
<220> FEATURE:
<223> OTHER INFORMATION: Synthetic construct

<400> SEQUENCE: 24
actcacgtta agggattttg gtcatga                                              27

<210> SEQ ID NO 25
<211> LENGTH: 27
<212> TYPE: DNA
<213> ORGANISM: Artificial Sequence
<220> FEATURE:
<223> OTHER INFORMATION: Synthetic construct

<400> SEQUENCE: 25
gcagaccatt atcgacaaaa tactcca                                              27

<210> SEQ ID NO 26
<211> LENGTH: 29
<212> TYPE: DNA
<213> ORGANISM: Artificial Sequence
<220> FEATURE:
<223> OTHER INFORMATION: Synthetic construct

<400> SEQUENCE: 26
cggaaatgtt gaatactcat actcttcct                                            29

<210> SEQ ID NO 27
<211> LENGTH: 5
<212> TYPE: PRT
<213> ORGANISM: Artificial Sequence
<220> FEATURE:
<223> OTHER INFORMATION: Synthetic construct

<400> SEQUENCE: 27

Gly Gly Gly Gly Ser
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic construct

<400> SEQUENCE: 28

Gly Gly Ser Gly
1

<210> SEQ ID NO 29
<211> LENGTH: 4
<212> TYPE: PRT
<213> ORGANISM: Artificial Sequence
<220> FEATURE:
<223> OTHER INFORMATION: Synthetic construct

<400> SEQUENCE: 29

Ser Gly Gly Gly
1

<210> SEQ ID NO 30
<211> LENGTH: 4
<212> TYPE: PRT
<213> ORGANISM: Artificial Sequence
<220> FEATURE:
<223> OTHER INFORMATION: Synthetic construct

<400> SEQUENCE: 30

Gly Ser Gly Ser
1

<210> SEQ ID NO 31
<211> LENGTH: 6
<212> TYPE: PRT
<213> ORGANISM: Artificial Sequence
<220> FEATURE:
<223> OTHER INFORMATION: Synthetic construct

<400> SEQUENCE: 31

Gly Ser Gly Ser Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct

<400> SEQUENCE: 32

Gly Ser Gly Ser Gly Ser Gly Ser
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic construct

<400> SEQUENCE: 33

Gly Ser Gly Ser Gly Ser Gly Ser Gly Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic construct

<400> SEQUENCE: 34

Gly Ser Gly Ser Gly Ser Gly Ser Gly Ser Gly Ser
1               5                   10

```
<210> SEQ ID NO 35
<211> LENGTH: 6
<212> TYPE: PRT
<213> ORGANISM: Artificial Sequence
<220> FEATURE:
<223> OTHER INFORMATION: Synthetic construct

<400> SEQUENCE: 35

Gly Gly Ser Gly Gly Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic construct

<400> SEQUENCE: 36

Gly Gly Ser Gly Gly Ser Gly Gly Ser
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic construct

<400> SEQUENCE: 37

Gly Gly Ser Gly Gly Ser Gly Gly Ser Gly Gly Ser
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthetic construct

<400> SEQUENCE: 38

Gly Gly Ser Gly Gly Gly Ser Gly
1               5

<210> SEQ ID NO 39
<211> LENGTH: 12
<212> TYPE: PRT
<213> ORGANISM: Artificial Sequence
<220> FEATURE:
<223> OTHER INFORMATION: Synthetic construct

<400> SEQUENCE: 39

Gly Gly Ser Gly Gly Gly Ser Gly Gly Gly Ser Gly
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Synthetic construct

<400> SEQUENCE: 40

Gly Gly Ser Gly Gly Gly Ser Gly Gly Gly Ser Gly Gly Gly Ser Gly
1               5                   10                  15

<210> SEQ ID NO 41
```

<211> LENGTH: 20
<212> TYPE: PRT
<213> ORGANISM: Artificial Sequence
<220> FEATURE:
<223> OTHER INFORMATION: Synthetic construct

<400> SEQUENCE: 41

Gly Gly Ser Gly Gly Gly Ser Gly Gly Gly Ser Gly Gly Gly Ser Gly
1               5                   10                  15
Gly Gly Ser Gly
            20

<210> SEQ ID NO 42
<211> LENGTH: 10
<212> TYPE: PRT
<213> ORGANISM: Artificial Sequence
<220> FEATURE:
<223> OTHER INFORMATION: Synthetic construct

<400> SEQUENCE: 42

Gly Gly Gly Gly Ser Gly Gly Gly Gly Ser
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Synthetic construct

<400> SEQUENCE: 43

Gly Gly Gly Gly Ser Gly Gly Gly Gly Ser Gly Gly Gly Gly Ser
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: Synthetic construct

<400> SEQUENCE: 44

Gly Ser Ala Gly Ser Ala Ala Gly Ser Gly Glu Phe
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct

<400> SEQUENCE: 45

Gly Glu Asn Leu Tyr Phe Gln Ser Gly Gly
1               5                   10

<210> SEQ ID NO 46
<211> LENGTH: 8
<212> TYPE: PRT
<213> ORGANISM: Artificial Sequence
<220> FEATURE:
<223> OTHER INFORMATION: Synthetic construct

<400> SEQUENCE: 46

Ser Ala Cys Tyr Cys Glu Leu Ser
1               5

FLUORESCENCE-BASED REPORTERS FOR MUTAGENESIS DETECTION IN *E. COLI*

CROSS REFERENCE TO RELATED APPLICATIONS

This application is the National Phase under 35 U.S.C. § 371 of PCT International Application No. PCT/US2017/068410 which has an international filing date of Dec. 26, 2017, and which claims priority to U.S. Provisional application No. 62/441,411, filed on Jan. 1, 2017, the entire contents of which are hereby incorporated.

STATEMENT OF SUPPORT

This disclosure was made with government support under the following grants: National Institute of Environmental Health Sciences) grant number RO1ES019625. The government has certain rights in the disclosure.

REFERENCE TO A "SEQUENCE LISTING" SUBMITTED AS ASCII TEXT FILE VIA EFS-WEB

The instant application contains a Sequence Listing which has been filed electronically in ASCII format and is hereby incorporated by reference in its entirety. Said ASCII copy, created on Feb. 15, 2018, is named 102913-000810US-1139880_SequenceListing.txt and is 29,669 bytes in size.

FIELD OF THE INVENTION

The disclosure relates to the direct detection of mutagenesis in prokaryotes using detection of reporter inactivation (forward mutation assay) and reversion of an inactivating mutation (reversion mutation assay).

BACKGROUND OF THE INVENTION

Mutagenesis following exposure to chemicals can be used to detect genotoxicity, which is an indicator of the potential of the chemical to cause cancer and/or birth defects. Mutagenesis assays are also used as a readout to study processes of DNA replication, DNA repair, DNA damage tolerization, and mechanisms of DNA homeostasis.

BRIEF SUMMARY OF THE INVENTION

Mutagenesis in model organisms following exposure to chemicals can be used as an indicator of genotoxicity. Mutagenesis assays can also be used to study mechanisms of DNA homeostasis. In prokaryotes, there are two approaches to the detection of mutagenesis: reporter inactivation (which is the basis for forward mutation assays) and reversion of an inactivating mutation (which occurs in reversion mutation assays). Both methods are labor-intensive and require visual screening, the quantification of colonies on solid media, or the determination of a Poisson distribution in liquid culture. Disclosed herein are reversion reporters that can be used to measure mutagenesis in vivo. These reporters produce a quantitative output. As a result, a mutagenesis assay using these reporters can be performed with a smaller amount of reagent, in less time, and with less labor. The assay involves a β lactamase (TEM-1)-based reversion assay and a fluorescent protein such as GFP or a derivative thereof.

Nucleic acids encoding the TEM-1 and the fluorescent protein can be provided on the same plasmid. Alternatively, they can be fused during protein translation with the N-terminus of the ORF interrupted using a stop codon. Also disclosed herein is a reporter that monitors continuous mutagenesis in mutator strains of bacteria. This reporter involves two reversion markers and has the benefit of allowing the detection of the two mutation events in real time. Disclosed are the reporter systems, methods of using the reporters, and a demonstration of key features of the reporters.

In one aspect, the disclosure features a method of detecting mutagenesis in *E. coli*, the method comprising: (a) culturing *E. coli* cells in a first liquid culture at a restrictive temperature, wherein the *E. coli* cells in the first liquid culture comprise a plasmid comprising (i) a first polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine, and (ii) a second polynucleotide encoding a fluorescent protein, wherein the first polynucleotide and the second polynucleotide are operably linked to a promoter; (b) plating the *E. coli* cells in the first liquid culture on a solid media comprising an antibiotic; (c) incubating the first solid media at a permissive temperature that allow the growth of *E. coli* colonies; (d) selecting a fluorescent *E. coli* colony from the solid media; (e) culturing the fluorescent *E. coli* colony in a second liquid culture at a permissive temperature, wherein the second liquid culture comprises the antibiotic; and (f) measuring the change in growth of the *E. coli* cells of the second culture relative to the first liquid culture, wherein the change in growth indicates mutagenesis of the inactive β-lactamase to an active β-lactamase.

In some embodiments of this aspect, nucleotides 202 to 204 of the sequence of any one of SEQ ID NOS: 2-7 encodes proline, threonine, arginine, a stop codon, or asparagine.

In another aspect, the disclosure features a method of detecting mutagenesis in *E. coli*, the method comprising: (a) culturing *E. coli* cells in a first liquid culture at a restrictive temperature, wherein the *E. coli* cells in the first liquid culture comprise a plasmid, wherein the plasmid comprises (i) a first polynucleotide encoding a non-fluorescent protein, and (ii) a second polynucleotide encoding an active β-lactamase, wherein the first polynucleotide and the second polynucleotide are operably linked to a promoter; (b) plating the *E. coli* cells in the first liquid culture on a solid media comprising an antibiotic; (c) incubating the first solid media at a permissive temperature that allow the growth of *E. coli* colonies; (d) selecting a fluorescent *E. coli* colony from the solid media; (e) culturing the fluorescent *E. coli* colony in a second liquid culture at a permissive temperature, wherein the second liquid culture comprises the antibiotic; and (f) measuring the change in fluorescence of the second liquid culture relative to the first liquid culture, wherein the change in fluorescence indicates mutagenesis of the non-fluorescent protein to a fluorescent protein.

In some embodiments of this aspect, the active β-lactamase has a sequence of SEQ ID NO: 8.

In another aspect, the disclosure features a method of detecting mutagenesis in *E. coli*, the method comprising: (a) culturing *E. coli* cells in a first liquid culture at a restrictive temperature, wherein the *E. coli* cells in the first liquid culture comprise a plasmid, wherein the plasmid comprises (i) a first polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine, and (ii) a second polynucleotide encoding a non-fluorescent protein, wherein the first polynucleotide and the second polynucleotide are operably linked to a promoter; (b) plating the *E. coli* cells in the first liquid culture on a first solid media comprising an antibiotic; (c) incubating the first solid media at a permissive temperature that allow the growth of *E. coli* colonies; (d) selecting a non-fluorescent *E. coli* colony from the first solid media; (e) culturing the non-fluorescent *E. coli* colony in a second liquid culture at a restrictive temperature, wherein the second liquid culture comprises the antibiotic; (f) plating the *E. coli* cells in the second liquid culture on a second solid media comprising the antibiotic; (g) incubating the second solid media at a permissive temperature that allow the growth of *E. coli* colonies; (h) selecting a fluorescent *E. coli* colony from the second solid media; (i) culturing the fluorescent *E. coli* colony in a third liquid culture at a permissive temperature, wherein the third liquid culture comprises the antibiotic; and (j) measuring the change in fluorescence of the third liquid culture relative to the first liquid culture, wherein the change in fluorescence indicates mutagenesis of the inactive β-lactamase to an active β-lactamase and of the non-fluorescent protein to a fluorescent protein.

In some embodiments of this aspect, nucleotides 202 to 204 of the sequence of any one of SEQ ID NOS: 2-7 encodes proline, threonine, arginine, a stop codon, or asparagine.

In some embodiments of any of the aspects above, the first polynucleotide is located 5' to the second polynucleotide in the plasmid. In some embodiments, the plasmid further comprises a linker between the first polynucleotide and the second polynucleotide. In particular embodiments, the linker may have a sequence of SEQ ID NO: 44.

In some embodiments, the antibiotic is a β-lactam antibiotic selected from the group consisting of kanamycin, carbenicillin, benzathine, benzylpenicillin, penicillin G, penicillin V, procaine, benzylpenicillin, cloxacillin, dicloxacillin, flucloxacillin, methicillin, nafcillin, oxacillin, temocillin, amoxicillin, ampicillin, mecillinam, carboxypenicillins, ticarcillin, ureidopenicillins, azlocillin, mezlocillin, piperacillin, cephalosporin C, cefoxitin, cephalosporin, cephamycin, cefazolin, cephalexin, cephalosporin C, cephalothin, cefaclor, cefamandole, cefuroxime, cefotetan, cefoxitin, cefixime, cefotaxime, cefpodoxime, ceftazidime, ceftriaxone, cefepime, cefpirome, ceftaroline, thienamycin, biapenem, doripenem, ertapenem, faropenem, imipenem, meropenem, panipenem, razupenem, tebipenem, and thienamycin. In particular embodiments, the antibiotic is kanamycin or carbenicillin.

In some embodiments of the aspects described herein, the β-lactamase is TEM-1.

In some embodiments, the fluorescent protein comprises GFP or a derivative thereof. In particular embodiments, the fluorescent protein comprises a sequence of any one of SEQ ID NOS: 9 and 10.

In some embodiments, the non-fluorescent protein comprises a sequence of SEQ ID NO: 11. In some embodiments, the non-fluorescent protein may be created by mutating codon ACT which encodes threonine at position 49 of SEQ ID NO: 9 to codon GCT which encodes alanine. In some embodiments, the non-fluorescent protein may be created by mutating codon TGC which encodes cysteine at position 48 of SEQ ID NO: 9 to codon TAC which encodes tyrosine. In some embodiments, the non-fluorescent protein may be created by mutating codon CCA which encodes proline at position 56 of SEQ ID NO: 9 to codon CTA which encodes leucine. In some embodiments, the non-fluorescent protein may be created by mutating codon GTC which encodes valine at position 61 of SEQ ID NO: 9 to codon GAC which encodes aspartic acid. In some embodiments, the non-fluorescent protein may be created by mutating codon ACT which encodes threonine at position 62 of SEQ ID NO: 9 to codon GCT which encodes alanine. In some embodiments, the non-fluorescent protein may be created by mutating codon CCC which encodes proline at position 89 of SEQ ID NO: 9 to codon TCC which encodes serine. In some embodiments, the non-fluorescent protein may be created by mutating codon GGT which encodes glycine at position 91 of SEQ ID NO: 9 to codon GAT which encodes aspartic acid. In some embodiments, the non-fluorescent protein may be created by mutating codon TAT which encodes tyrosine at position 92 of SEQ ID NO: 9 to codon TGT which encodes cysteine. In some embodiments, the non-fluorescent protein may be created by mutating codon GAC which encodes aspartic acid at position 103 of SEQ ID NO: 9 to codon GTC which encodes valine. In some embodiments, the non-fluorescent protein may be created by mutating codon TAC which encodes tyrosine at position 143 of SEQ ID NO: 9 to codon TGC which encodes cysteine. In some embodiments, the non-fluorescent protein may be created by mutating codon CAA which encodes glutamine at position 183 of SEQ ID NO: 9 to codon CAC which encodes histidine. In some embodiments, the non-fluorescent protein may be created by mutating codon GAA which encodes glutamic acid at position 213 of SEQ ID NO: 9 to codon GGA which encodes glycine.

In some embodiments of the aspects of the disclosure, the first polynucleotide and the second polynucleotide are expressed as a fusion protein. In some embodiments, the fusion protein comprises a sequence of SEQ ID NO: 12.

In some embodiments, the methods further comprise exposing the *E. coli* cells to a test compound added to the first liquid culture and/or second liquid culture. In some embodiments, the test compound is a mutagen.

In another aspect, the disclosure features a kit comprising a plasmid comprising (i) a first polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine, and (ii) a second polynucleotide encoding a fluorescent protein, wherein the first polynucleotide and the second polynucleotide are operably linked to a promoter.

In some embodiments of this aspect, nucleotides 202 to 204 of the sequence of any one of SEQ ID NOS: 2-7 encodes proline, threonine, arginine, a stop codon, or asparagine.

In another aspect, the disclosure features a kit comprising a plasmid comprising (i) a first polynucleotide encoding a non-fluorescent protein, and (ii) a second polynucleotide encoding an active β-lactamase, wherein the first polynucleotide and the second polynucleotide are operably linked to a promoter.

In another aspect, the disclosure features a kit comprising a plasmid comprising (i) a first polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine, and (ii) a second polynucleotide encoding a non-fluorescent protein, wherein the first polynucleotide and the second polynucleotide are operably linked to a promoter.

In some embodiments of this aspect, nucleotides 202 to 204 of the sequence of any one of SEQ ID NOS: 2-7 encodes proline, threonine, arginine, a stop codon, or asparagine.

In another aspect, the disclosure features a kit comprising *E coli* cells transformed with a plasmid comprising (i) a first polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine, and (ii) a second polynucleotide encoding a fluorescent protein, wherein the first polynucleotide and the second polynucleotide are operably linked to a promoter.

In some embodiments of this aspect, nucleotides 202 to 204 of the sequence of any one of SEQ ID NOS: 2-7 encodes proline, threonine, arginine, a stop codon, or asparagine.

In another aspect, the disclosure features a kit comprising *E coli* cells transformed with a plasmid comprising (i) a first polynucleotide encoding a non-fluorescent protein, and (ii) a second polynucleotide encoding an active β-lactamase, wherein the first polynucleotide and the second polynucleotide are operably linked to a promoter.

In another aspect, the disclosure features a kit comprising *E coli* cells transformed with a plasmid comprising (i) a first polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine, and (ii) a second polynucleotide encoding a non-fluorescent protein, wherein the first polynucleotide and the second polynucleotide are operably linked to a promoter.

In some embodiments of this aspect, nucleotides 202 to 204 of the sequence of any one of SEQ ID NOS: 2-7 encodes proline, threonine, arginine, a stop codon, or asparagine.

In some embodiments, the *E. coli* cells in the kit are of a mutator strain and/or a readout strain.

In some embodiments, the first polynucleotide is located 5' to the second polynucleotide in the plasmid.

In some embodiments, the plasmid further comprises a linker between the first polynucleotide and the second polynucleotide. In particular embodiments, the link has a sequence of SEQ ID NO: 44.

In some embodiments, the β-lactamase is TEM-1.

In some embodiments of the aspects directed to kits of the disclosure, the fluorescent protein comprises GFP or a derivative thereof. In particular embodiments, the fluorescent protein comprises a sequence of SEQ ID NOS: 9 and 10.

In some embodiments of the aspects directed to kits of the disclosure, the non-fluorescent protein comprises a sequence of SEQ ID NO: 11. In some embodiments, the non-fluorescent protein may be created by mutating codon ACT which encodes threonine at position 49 of SEQ ID NO: 9 to codon GCT which encodes alanine. In some embodiments, the non-fluorescent protein may be created by mutating codon TGC which encodes cysteine at position 48 of SEQ ID NO: 9 to codon TAC which encodes tyrosine. In some embodiments, the non-fluorescent protein may be created by mutating codon CCA which encodes proline at position 56 of SEQ ID NO: 9 to codon CTA which encodes leucine. In some embodiments, the non-fluorescent protein may be created by mutating codon GTC which encodes valine at position 61 of SEQ ID NO: 9 to codon GAC which encodes aspartic acid. In some embodiments, the non-fluorescent protein may be created by mutating codon ACT which encodes threonine at position 62 of SEQ ID NO: 9 to codon GCT which encodes alanine. In some embodiments, the non-fluorescent protein may be created by mutating codon CCC which encodes proline at position 89 of SEQ ID NO: 9 to codon TCC which encodes serine. In some embodiments, the non-fluorescent protein may be created by mutating codon GGT which encodes glycine at position 91 of SEQ ID NO: 9 to codon GAT which encodes aspartic acid. In some embodiments, the non-fluorescent protein may be created by mutating codon TAT which encodes tyrosine at position 92 of SEQ ID NO: 9 to codon TGT which encodes cysteine. In some embodiments, the non-fluorescent protein may be created by mutating codon GAC which encodes aspartic acid at position 103 of SEQ ID NO: 9 to codon GTC which encodes valine. In some embodiments, the non-fluorescent protein may be created by mutating codon TAC which encodes tyrosine at position 143 of SEQ ID NO: 9 to codon TGC which encodes cysteine. In some embodiments, the non-fluorescent protein may be created by mutating codon CAA which encodes glutamine at position 183 of SEQ ID NO: 9 to codon CAC which encodes histidine. In some embodiments, the non-fluorescent protein may be created by mutating codon GAA which encodes glutamic acid at position 213 of SEQ ID NO: 9 to codon GGA which encodes glycine.

In some embodiments of the aspects directed to kits of the disclosure, the first polynucleotide and the second polynucleotide are expressed as a fusion protein. In particular embodiments, the fusion protein comprises a sequence of SEQ ID NO: 12.

Definitions

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand.

As used herein, the term "promoter" refers to a polynucleotide sequence capable of driving transcription of a coding sequence in a cell. Thus, promoters may include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription.

As used herein, the term "plasmid" refers to an extrachromosomal circular DNA capable of autonomous replication in a given cell. In certain embodiments, the plasmid is designed for amplification and expression in bacteria (e.g., *E. coli*). Plasmids can be engineered by standard molecular biology techniques. See Sambrook et al. Laboratory Manual, Cold Spring Harbor Laboratory Press, Cold Spring Harbor (1989), N.Y. A plasmid may be a recombinant DNA molecule containing a desired coding sequence and appropriate nucleic acid sequences necessary for expression of the operably linked coding sequence in a particular host cell. Nucleic acid sequences necessary for expression in prokaryotes usually include a promoter, an operator (optional), and a ribosome binding site, often along with other sequences.

As used herein, the term "operably linked" refers to nucleic acid sequences or proteins that are placed into a functional relationship with another nucleic acid sequence or protein. For example, a promoter sequence is operably linked to a coding sequence (e.g., the first polynucleotide and the second polynucleotide in a plasmid) if the promoter promotes transcription of the coding sequence. Generally, "operably linked" means that the DNA sequences being linked are contiguous, although they need not be, and that a gene and a regulatory sequence (e.g., a promoter) are connected in such a way as to permit gene expression.

As used herein, the term "percent (%) sequence identity" refers to the percentage of nucleic acid or amino acid residues of a candidate sequence that are identical to the nucleic acid or amino acid residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent nucleic acid or amino acid sequence identity of a given candidate sequence to, with, or against a given reference sequence (which can alternatively be phrased as a given candidate sequence that has or includes a certain percent nucleic acid or amino acid sequence identity to, with, or against a given reference sequence) is calculated as follows:

$$100 \times (\text{fraction of A/B})$$

where A is the number of nucleic acid or amino acid residues scored as identical in the alignment of the candidate sequence and the reference sequence, and where B is the total number of nucleic acid or amino acid residues in the reference sequence. In some embodiments where the length of the candidate sequence does not equal to the length of the reference sequence, the percent nucleic acid or amino acid sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous nucleic acid or amino acid residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same nucleic acid or amino acid residue as the corresponding position in the reference sequence, then the molecules are identical at that position.

For example, as described herein, a plasmid in methods of the disclosure may comprise a polynucleotide encoding an inactive β-lactamase and having at least 90% sequence identity to a sequence of any one of SEQ ID NOS: 2-7, wherein nucleotides 202 to 204 of the sequence of any one of SEQ ID NOS: 2-7 does not encode serine. In some embodiments, the polynucleotide encoding the inactive β-lactamase may have at least 90% sequence identity to a sequence of any one of SEQ ID NOS: 2-7, wherein nucleotides 202 to 204 of the sequence of any one of SEQ ID NOS: 2-7 does not encode serine. This may be interpreted as, i.e., the polynucleotide encoding an inactive β-lactamase may be translated to the same protein sequence as that encoded by any one of SEQ ID NOS: 2-7, but the polynucleotide may contain silent nucleotide mutations compared to the sequence of any one of SEQ ID NOS: 2-7, where the silent nucleotide mutations do not change the amino acids encoded by the polynucleotide.

As used herein, the term "mutagenesis" refers a process in which the genetic make-up of an organism (e.g., bacteria) is changed. In some embodiments, mutagenesis may be induced by certain environmental conditions, i.e., growing *E. coli* cells at a restrictive temperature and/or adding a mutagen in the cell culture.

As used herein, the term "solid media" refers a cell culture media that is solid or semi-sold (e.g., a gel) and contains nutritional elements bacteria need for growth. In some embodiments, the solid media may also contain certain selective markers, e.g., an antibiotic. In some embodiments, a solid media may be made from Luria-Bertani broth (LB broth).

As used herein, the term "restrictive temperature" refers to a temperature that leads to an increase mutagenic frequency and acts as a selective pressure for the *E. coli* cells. In some embodiments, restrictive temperature may be about 37° C. In some embodiments, a reversion event is more likely to occur under restrictive temperature. For example, an inactive β-lactamase having a S68P mutation may undergo a reversion event back to an active β-lactamase having serine at position 68 instead of proline.

As used herein, the term "permissive temperature" refers to a temperature allows or encourages the normal growth of *E. coli* cells, without causing increase mutagenesis in the *E. coli* cells. In some embodiments, restrictive temperature may be about 30° C.

As used herein, the term "fluorescent protein" refers to a protein that exhibits low, medium, or intense fluorescence upon irradiation with light of the appropriate excitation wavelength. The fluorescent characteristic of fluorescent protein is one that arises from the chromophore, wherein the chromophore results from autocatalytic cyclization of two or more amino acid residues of the protein.

As used herein, the term "non-fluorescent protein" refers to a protein that can become fluorescent upon a reversion event. A non-fluorescent protein may be constructed by mutating one or more nucleotides or one or more amino acids of a fluorescent protein. Once the mutated nucleotide or amino acid is returned to the non-mutated version (the nucleotide or amino acid present in the initial fluorescent protein) after a reversion event, the non-fluorescent protein can become fluorescent again.

As used herein, the term "mutagen" refers to a chemical agent that causes changes in the genetic make-up of an organism (e.g., bacteria) and increases the mutagenic frequency.

kanamycin resistance (opposite orientation) 3400-2575; and lactamase fragment 3553-3851. (C) Negative control not bearing the TEM1 gene.

Figure 2A:
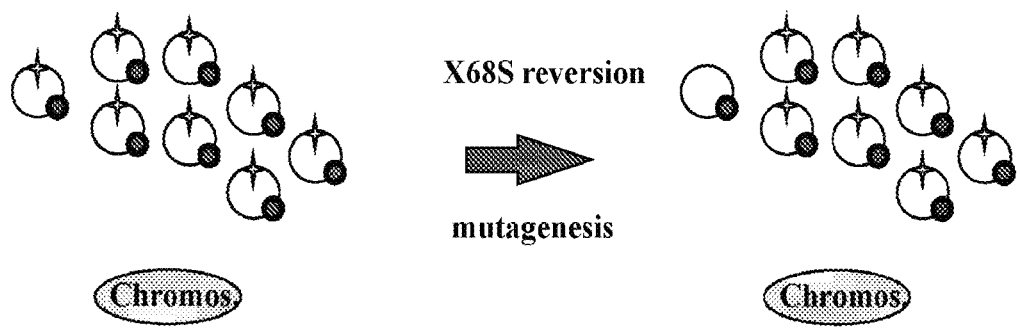
Figure 2A:
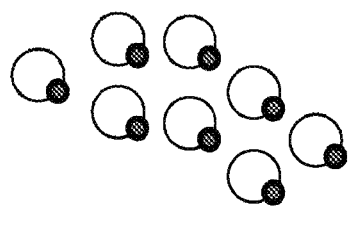
Figure 2A:
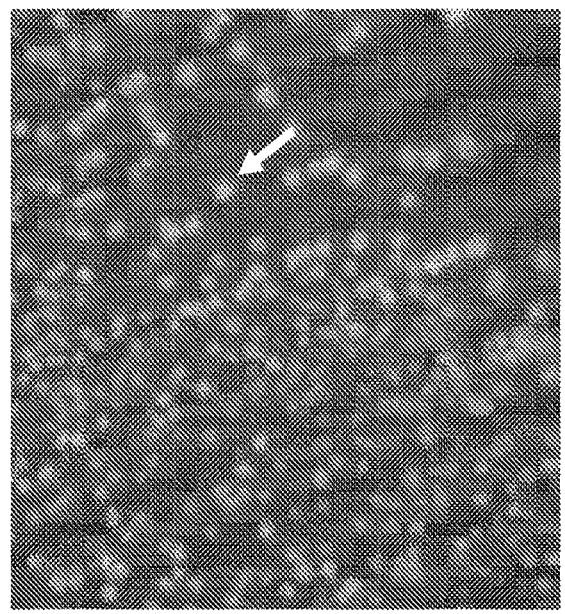
Figure 2B:
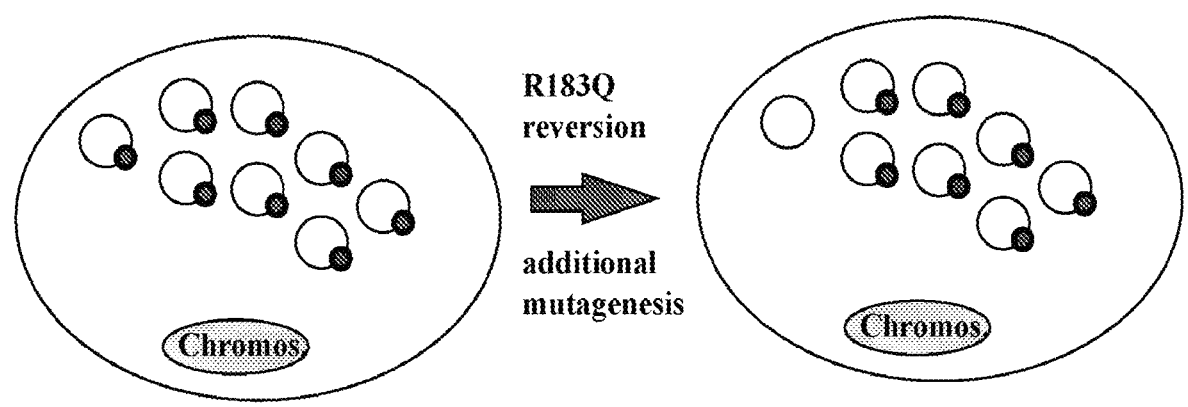
Figure 2B:
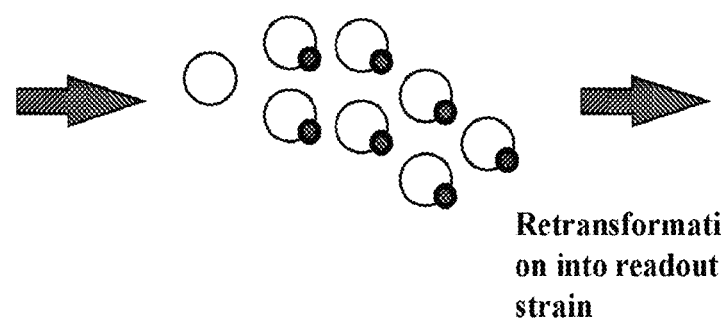
Figure 2B:
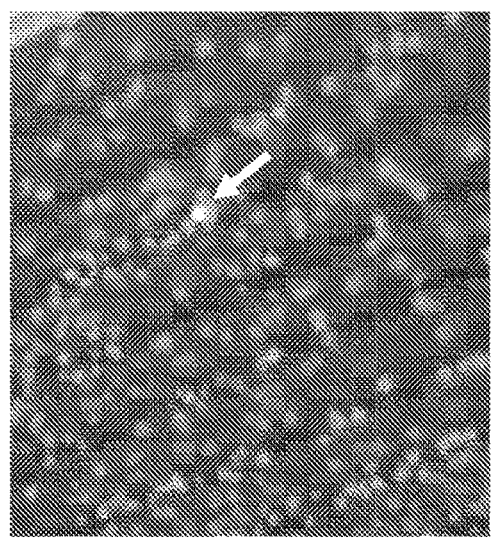

FIGS. 2A and 2B: Methods for detection of two mutations separated in time. Colonies representing reversions in TEM1 β-lactamase were expanded under restrictive (mutagenic) conditions, their plasmid pools were recovered through miniprep and retransformed. The two reversion reporters are shown as star (S68X) and circle (Q183R). (A) Detection of first mutation: once reversion at the S68X site occurs under selective pressure, the reversion events get amplified, representing a majority of the plasmid population and leading to carbenicillin resistance. (B) Detection of second mutation: single, carbenicillin-resistant colonies (white arrow) are grown. Plasmids from these cultures are recovered. Reversions at the Q183 site of the GFP reporter are detected by retransformation of recovered plasmids into a readout strain, producing fluorescent colonies (white arrow) on a background on non-fluorescent ones. The frequency of reversion can be used to estimate rate of mutagenesis.

Figure 3A:
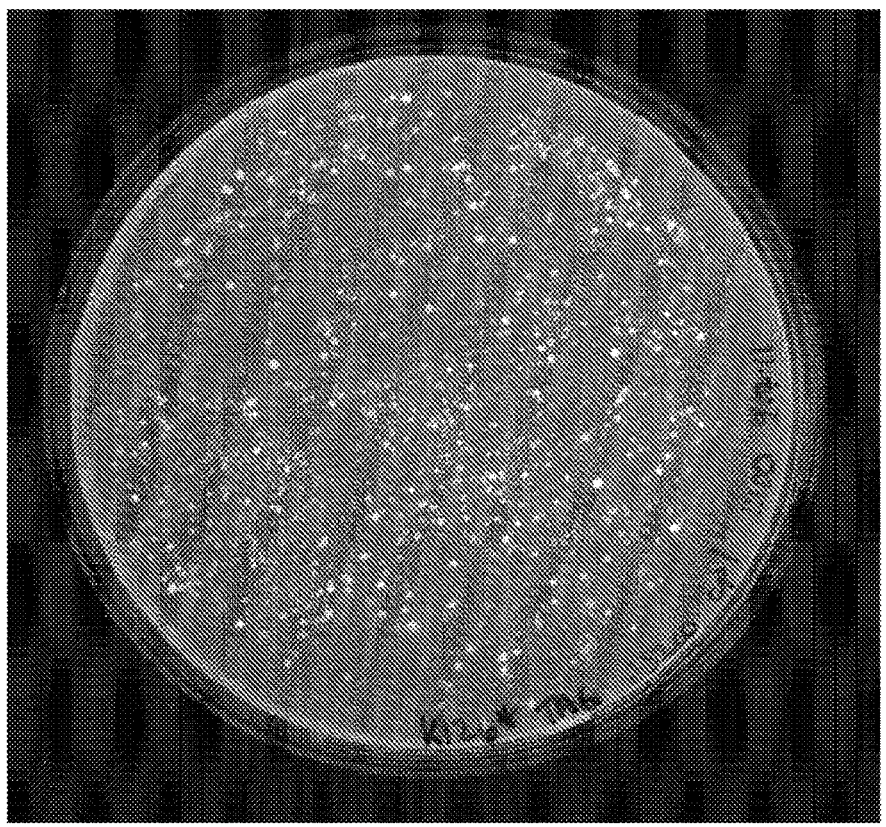
Figure 3B:
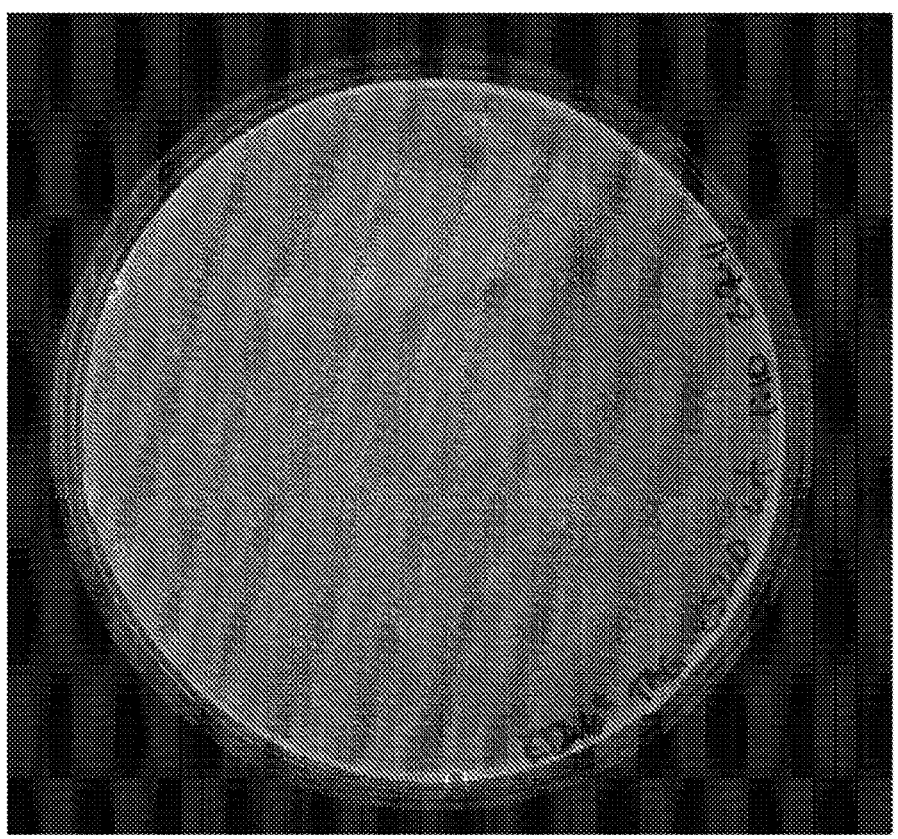

FIGS. 3A and 3B: sfGFPrev-TEM reporter containing the mutation K126stop in sfGFPrev on solid plates. Following Pol I mutagenesis, cells were plated on LB carbenicillin. (A) Plasmids recovered from cells expressing LF-Pol I. (B) Plasmids recovered from cells expressing WT Pol I (control).

Figure 4A:
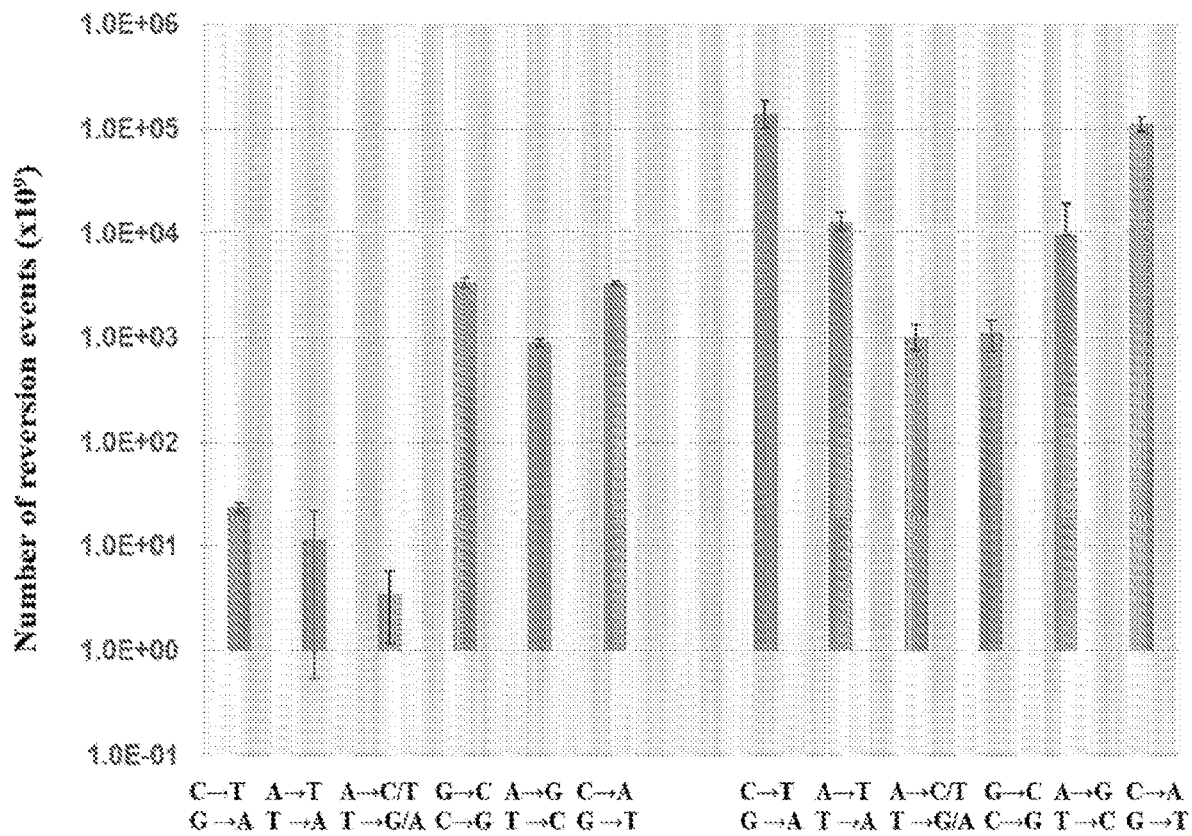
Figure 4B:
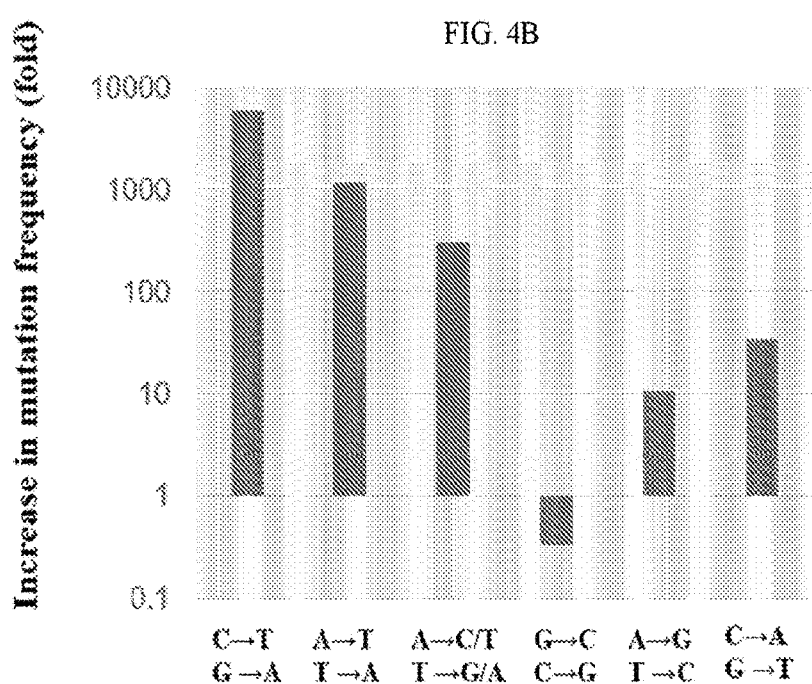

FIGS. 4A and 4B: LF-Pol I reversion profile. The set of six S68X reporters was transformed in JS200 cells expressing LF-Pol I and error-prone reporter plasmid replication was performed as described in methods. As a control, the same reporters were transformed into JS200 cells expressing WT Pol 1. (A) Original reversion frequencies in log scale. Error bars represent standard deviation of triplicates. (B) Reversion frequency relative to control cells expressing WT polymerase I (fold, in log scale)

FIGS. 5A-5D: Mutagenesis assay in 96-well format. Cells bearing two sample reporters, S68P (which detects C:G→T:A mutations) or S68R1 (which detects A:T→C:G and A:T→T:A mutations) underwent error-prone plasmid replication as described in the examples. Cells were recovered by washing the plates and inoculated into 96-deep-well plates to a final OD of 0.5. At different time points (shown in the X-axis) samples were drawn and kept at 4° C. After completion of the time-course, fluorescence and optical density ($OD_{600}$) were measured. LF-Pol I mutagenesis, triangles; WT Pol I control, squares, negative control with no β-lactamase gene, circles. (A) S68P reporter, $OD_{600}$, in log scale. (B) S68R1 reporter, $OD_{600}$, in log scale. (C) S68P reporter, fluorescence. (D) S68R1 reporter, fluorescence. Error bars represent variation between duplicates.

Figure 6:
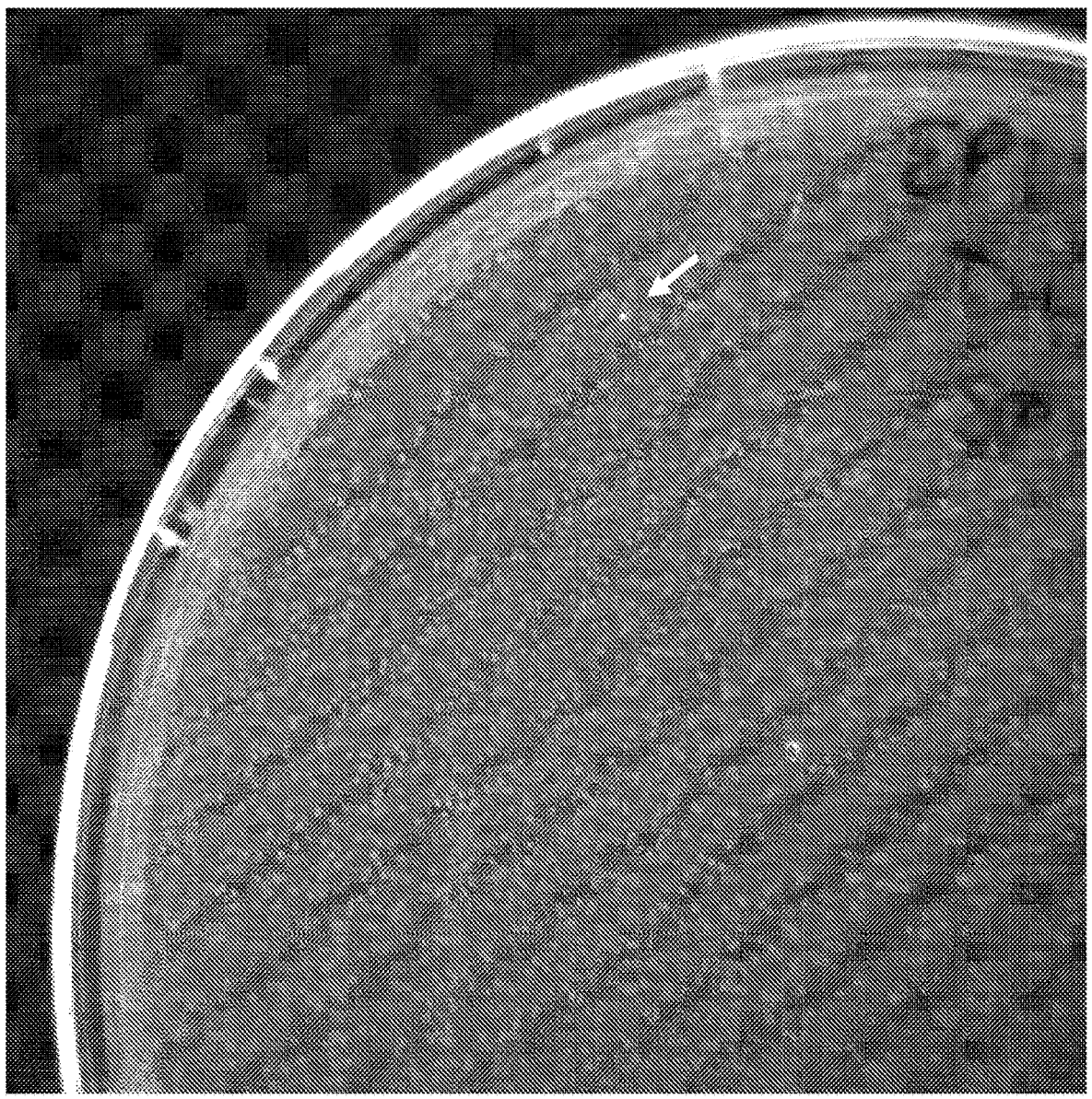

FIG. 6: Q183R reporter: R183Q reversion on a plate containing 9400 colonies is shown. Transformation in DH5α cells (readout strain) of plasmids recovered from expansion in liquid culture of a non-fluorescent carbenicillin-resistant colony and grown under continuous mutagenesis conditions (diagrammed in FIGS. 2A and 2B). No revertants were seen in 73,500 transformants from plasmids recovered in cells expressing WT polymerase grown under the same conditions.

DETAILED DESCRIPTION OF THE INVENTION

The present disclosure encompasses reporter constructs used for the direct detection of mutagenesis in prokaryotes. In some embodiments, the reporter constructs use transcriptional coupling of β-lactamase (TEM-1) reversion and a fluorescent protein (e.g., GFP). The reporter constructs may also employ translational fusion between β-lactamase (TEM-1) and a fluorescent protein (e.g., GFP) containing a stop codon. In other embodiments, the reporter constructs may be designed to monitor continuous mutagenesis and measure the mutagenesis rate in a mutator strain. The reporters described herein produce a quantitative output, and therefore can reduce the amount of test compounds and labor involved in the performance of mutagenesis assays.

I. Mutagenesis Assays

Mutagenesis may be detected directly or indirectly. Direct detection of mutagenesis can be performed in prokaryotes. Genotoxicity can also be detected indirectly, through transcriptional fusion of a reporter gene to a promoter that is indicative of DNA damage, such as genes belonging to the SOS response (umuDC, sulA, recN, recA), alkA, or nrdA. Genotoxicity can also be detected physically by detecting DNA damage (breaks or rearrangements) using, e.g., Comet assay. In addition to prokaryotic systems, a variety of eukaryotic organisms, notably yeast, Drosophila, and mouse, have been used.

Relative to indirect methods of mutagenesis detection in prokaryotes, mutagenesis assays have the advantage of being able to detect specific changes in DNA sequence rather than all DNA damage-induced alterations in gene expression. Compared to eukaryotic model systems, bacterial assays are fast and cheap, but cannot detect mutagenesis in targets not conserved between prokaryotes and eukaryotes (such as cytoskeleton, nucleotide excision repair targets). Bacterial assays also cannot detect bioactivation as accurately. Still, direct mutagenesis assays in bacteria constitute one of three assays required by regulatory agencies for the demonstration of safety for potential clinical compounds. The other two assays required are related to a eukaryotic cell culture test and an animal test.

General approaches for detecting mutagenesis in prokaryotes include reporter inactivation (measured in a forward mutation assay) and reversion of an inactivating mutation (measured in a reversion mutation assay). Both the forward mutation assay and the reversion mutation assay are labor-intensive, involving visual screening, quantification of colonies on solid media, and/or obtaining a Poisson distribution in liquid culture. Forward mutation assays are based on the inactivation of a reporter. Reporters can produce colorimetric (e.g., galK, lacZ, luciferase), luminescent, fluorescent (e.g., GFP), or electrochemical signals. Inactivation can result from a variety of mutations. Thus, compared to reversion assays, forward mutation assays detect events that are more frequent. Forward mutation assays also provide a more accurate representation of the range of genetic changes induced by the relevant mutagen because inactivation is generally not dependent on a specific mutation occurring. In some cases, the readout for these involves a survival marker, e.g., a gene that confers resistance to a drug or to the presence or absence of a nutrient. RpoB (a gene encoding for RNA polymerase) is an example, as mutations in a variety of loci produce resistance to rifampin. AraD is another example. The cells used in this assay have a mutation in the araD gene, which results in the accumulation of a toxic intermediate when arabinose is present in the growth media. Mutations upstream of the araD gene that inactivate the operon prevent the metabolism of arabinose, causing the accumulation of the toxic intermediate and making cells resistant to arabinose. Sectoring, which detects inactivation of a reporter within a colony as an indication of high and continuous mutation rates, is another variant of a forward mutation assay. Forward mutation assays are often more labor-intensive because they require screening.

Reversion assays detect when a known inactivating mutation at a pre-determined site is reverted to wild type, typically through a selection (auxotrophy, antibiotic resistance, FACS sorting). The availability of selection increases the sensitivity of these assays relative to the forward mutation assays described above and the reversion assays can also accurately detect a specific mutation. However, the dependence of reversion assays on individual mutations at pre-determined sites makes them susceptible to sequence context effects and limits the range of genetic changes that can be detected. The readout for such an assay can be any of the signals described above (e.g., colorimetric, luminescent, fluorescent, or electrochemical signals). The Ames Test was the first reversion assay to be developed and it is still by far the most widely-used method for testing mutagenesis in prokaryotes. The Ames Test detects the reversion of a mutation that prevents the biosynthesis of histidine and allows the growth of bacteria on solid agar in the presence of trace amounts of histidine. A set of six strains has been developed to detect a broad range of point mutations and frameshift mutations. Two further variations have been developed to facilitate high-throughput formatting and to reduce the amount of sample needed. The Mini-Ames Test follows the standard Ames Test protocol, except at a smaller size. The Ames Fluctuation Test is performed in liquid culture, with the mutation detected by a chromophore that indicates growth. Reversion assays based on TEM β-lactamase have also been developed and one of the assays includes a set of six point mutations reporting on each type of point mutation that is possible in double-stranded DNA. All these reversion assays produce a binary output, i.e., growth vs. no growth. As a result, determining the mutagenicity or genotoxicity of a single concentration of a test compound requires fine-tuning the dose and serial dilutions to obtain countable colonies on solid plates or a sufficient number of positive wells that follow a Poisson distribution in a liquid culture.

Another type of reversion assay is the papillation assay, which can be used to detect alterations in mutagenesis rates in vivo. This assay is based on a mutation in the gal2K gene, which renders cells unable to ferment galactose. Cells are grown on Mac-Conkey-galactose plates, producing white colonies. Spottings on the surface of these colonies, often referred to as colored papilla (sectors), represent microcolonies derived from a single Gal+ mutant capable of galactose fermentation. The output is only semi-quantitative as it depends on mutation events occurring early enough to allow for visual detection.

Mutator strains are bacterial strains that consistently exhibit an elevated mutation frequency and can be identified by their ability to produce sectored colonies. There are some indications that the mutation rates in mutator strains are not constant, as there is a counter-selection against high mutation rates due to the deleterious and/or adaptive effects of mutations. In addition, studying the dynamics of mutagenesis in mutator strains using reporters is difficult because mutations can inactivate the reporter regardless of its forward or reversion status with a probability that grows exponentially with the number of mutations present.

II. Revision Reporters

Disclosed are reporter systems that can be used to detect and quantify point mutations. These reporters are provided on a plasmid comprising a pMB1 (ColE1-like) plasmid origin of replication. This has several advantages over a chromosomal location: (1) a plasmid reporter increases the number of targets for mutagenesis by at least one order of magnitude, since ColE1 plasmids are multicopy plasmids; (2) the fact that plasmids are present in multiple copies also allows amplification of reporter signal through selection; and (3) a plasmid reporter facilitates exposure to mutagens ex vivo, in this scenario, transformation would be performed only to obtain a readout.

TEM-1

TEM-1 is a type of β-lactamase found in Gram-negative bacteria. Expression of TEM-1 confers resistance to carbenicillin, as well as other β-lactam antibiotics such as penicillin. The version of TEM-1 used the reporters as disclosed herein can be inactivated through mutations in the S68 position of the protein. S68 is a serine residue that polarizes the carbonyl group of the β-lactam amide bond in the β-lactam ring of β-lactamase antibiotics and is completely intolerant to amino acid changes. A set of six TEM-1 constructs with nucleotide point mutations at S68 was engineered such that each nucleotide point mutation is within the serine-coding codon (nucleotides 202 to 204 ("AGC") of SEQ ID NO: 1 encodes for serine). As a result, each of the 6 pairs of nucleotide substitutions that are possible in duplex DNA can be detected. Point mutations at this position were engineered to be one nucleotide away from a serine-coding codon so that each of the 6 pairs of nucleotide substitutions that are possible in duplex DNA can be detected. Table 1 below lists the nucleotide sequence of wild-type TEM-1 (SEQ ID NO: 1), the nucleotide sequences encoding the six TEM-1 constructs with mutations at S68 codon (SEQ ID NOS: 2-7), and the protein sequence of wild-type TEM-1 (SEQ ID NO: 8).

TABLE 1

```
SEQ ID NO: 1 (nucleotide sequence encoding wild-type TEM-1)
   1 ATGAGTATTC AACATTTCCG TGTCGCCCTT ATTCCCTTTT TTGCGGCATT TTGCCTTCCT
  61 GTTTTTGCTC ACCCAGAAAC GCTGGTGAAA GTAAAAGATG CTGAAGATCA GTTGGGTGCA
 121 CGAGTGGGTT ACATCGAACT GGATCTCAAC AGCGGTAAGA TCCTTGAGAG TTTTCGCCCC
 181 GAAGAACGTT TTCCAATGAT GAGCACTTTT AAAGTTCTGC TATGTGGCGC GGTATTATCC
 241 CGTATTGACG CCGGGCAAGA GCAACTCGGT CGCCGCATAC ACTATTCTCA GAATGACTTG
 301 GTTGAGTACT CACCAGTCAC AGAAAAGCAT CTTACGGATG GCATGACAGT AAGAGAATTA
 361 TGCAGTGCTG CCATAACCAT GAGTGATAAC ACTGCGGCCA ACTTACTTCT GACAACGATC
 421 GGAGGACCGA AGGAGCTAAC CGCTTTTTTG CACAACATGG GGGATCATGT AACTCGCCTT
 481 GATCGTTGGG AACCGGAGCT GAATGAAGCC ATACCAAACG ACGAGCGTGA CACCACGATG
 541 CCTGTAGCAA TGGCAACAAC GTTGCGCAAA CTATTAACTG GCGAACTACT TACTCTAGCT
 601 TCCCGGCAAC AATTAATAGA CTGGATGGAG GCGGATAAAG TTGCAGGACC ACTTCTGCGC
 661 TCGGCCCTTC CGGCTGGCTG GTTTATTGCT GATAAATCTG GAGCCGGTGA GCGTGGGTCT
 721 CGCGGTATCA TTGCAGCACT GGGGCCAGAT GGTAAGCCCT CCCGTATCGT AGTTATCTAC
 781 ACGACGGGGA GTCAGGCAAC TATGGATGAA CGAAATAGAC AGATCGCTGA GATAGGTGCC
 841 TCACTGATTA AGCATTGGTA A
```

TABLE 1-continued

```
SEQ ID NO: 2 (nucleotide sequence encoding TEM-1(S68P))
  1 ATGAGTATTC AACATTTCCG TGTCGCCCTT ATTCCCTTTT TTGCGGCATT TTGCCTTCCT
 61 GTTTTTGCTC ACCCAGAAAC GCTGGTGAAA GTAAAAGATG CTGAAGATCA GTTGGGTGCA
121 CGAGTGGGTT ACATCGAACT GGATCTCAAC AGCGGTAAGA TCCTTGAGAG TTTTCGCCCC
181 GAAGAACGTT TTCCAATGAT GCCAACTTTT AAAGTTCTGC TATGTGGCGC GGTATTATCC
241 CGTATTGACG CCGGGCAAGA GCAACTCGGT CGCCGCATAC ACTATTCTCA GAATGACTTG
301 GTTGAGTACT CACCAGTCAC AGAAAAGCAT CTTACGGATG GCATGACAGT AAGAGAATTA
361 TGCAGTGCTG CCATAACCAT GAGTGATAAC ACTGCGGCCA ACTTACTTCT GACAACGATC
421 GGAGGACCGA AGGAGCTAAC CGCTTTTTTG CACAACATGG GGGATCATGT AACTCGCCTT
481 GATCGTTGGG AACCGGAGCT GAATGAAGCC ATACCAAACG ACGAGCGTGA CACCACGATG
541 CCTGTAGCAA TGGCAACAAC GTTGCGCAAA CTATTAACTG GCGAACTACT TACTCTAGCT
601 TCCCGGCAAC AATTAATAGA CTGGATGGAG GCGGATAAAG TTGCAGGACC ACTTCTGCGC
661 TCGGCCCTTC CGGCTGGCTG GTTTATTGCT GATAAATCTG GAGCCGGTGA GCGTGGGTCT
721 CGCGGTATCA TTGCAGCACT GGGGCCAGAT GGTAAGCCCT CCCGTATCGT AGTTATCTAC
781 ACGACGGGGA GTCAGGCAAC TATGGATGAA CGAAATAGAC AGATCGCTGA GATAGGTGCC
841 TCACTGATTA AGCATTGGTA A SEQ ID NO: 3 (nucleotide sequence encoding TEM-1(S68T))
  1 ATGAGTATTC AACATTTCCG TGTCGCCCTT ATTCCCTTTT TTGCGGCATT TTGCCTTCCT
 61 GTTTTTGCTC ACCCAGAAAC GCTGGTGAAA GTAAAAGATG CTGAAGATCA GTTGGGTGCA
121 CGAGTGGGTT ACATCGAACT GGATCTCAAC AGCGGTAAGA TCCTTGAGAG TTTTCGCCCC
181 GAAGAACGTT TTCCAATGAT GACAACTTTT AAAGTTCTGC TATGTGGCGC GGTATTATCC
241 CGTATTGACG CCGGGCAAGA GCAACTCGGT CGCCGCATAC ACTATTCTCA GAATGACTTG
301 GTTGAGTACT CACCAGTCAC AGAAAAGCAT CTTACGGATG GCATGACAGT AAGAGAATTA
361 TGCAGTGCTG CCATAACCAT GAGTGATAAC ACTGCGGCCA ACTTACTTCT GACAACGATC
421 GGAGGACCGA AGGAGCTAAC CGCTTTTTTG CACAACATGG GGGATCATGT AACTCGCCTT
481 GATCGTTGGG AACCGGAGCT GAATGAAGCC ATACCAAACG ACGAGCGTGA CACCACGATG
541 CCTGTAGCAA TGGCAACAAC GTTGCGCAAA CTATTAACTG GCGAACTACT TACTCTAGCT
601 TCCCGGCAAC AATTAATAGA CTGGATGGAG GCGGATAAAG TTGCAGGACC ACTTCTGCGC
661 TCGGCCCTTC CGGCTGGCTG GTTTATTGCT GATAAATCTG GAGCCGGTGA GCGTGGGTCT
721 CGCGGTATCA TTGCAGCACT GGGGCCAGAT GGTAAGCCCT CCCGTATCGT AGTTATCTAC
781 ACGACGGGGA GTCAGGCAAC TATGGATGAA CGAAATAGAC AGATCGCTGA GATAGGTGCC
841 TCACTGATTA AGCATTGGTA A SEQ ID NO: 4 (nucleotide sequence encoding TEM-1(S68R1))
  1 ATGAGTATTC AACATTTCCG TGTCGCCCTT ATTCCCTTTT TTGCGGCATT TTGCCTTCCT
 61 GTTTTTGCTC ACCCAGAAAC GCTGGTGAAA GTAAAAGATG CTGAAGATCA GTTGGGTGCA
121 CGAGTGGGTT ACATCGAACT GGATCTCAAC AGCGGTAAGA TCCTTGAGAG TTTTCGCCCC
181 GAAGAACGTT TTCCAATGAT GAGAACTTTT AAAGTTCTGC TATGTGGCGC GGTATTATCC
241 CGTATTGACG CCGGGCAAGA GCAACTCGGT CGCCGCATAC ACTATTCTCA GAATGACTTG
301 GTTGAGTACT CACCAGTCAC AGAAAAGCAT CTTACGGATG GCATGACAGT AAGAGAATTA
361 TGCAGTGCTG CCATAACCAT GAGTGATAAC ACTGCGGCCA ACTTACTTCT GACAACGATC
421 GGAGGACCGA AGGAGCTAAC CGCTTTTTTG CACAACATGG GGGATCATGT AACTCGCCTT
481 GATCGTTGGG AACCGGAGCT GAATGAAGCC ATACCAAACG ACGAGCGTGA CACCACGATG
541 CCTGTAGCAA TGGCAACAAC GTTGCGCAAA CTATTAACTG GCGAACTACT TACTCTAGCT
601 TCCCGGCAAC AATTAATAGA CTGGATGGAG GCGGATAAAG TTGCAGGACC ACTTCTGCGC
661 TCGGCCCTTC CGGCTGGCTG GTTTATTGCT GATAAATCTG GAGCCGGTGA GCGTGGGTCT
721 CGCGGTATCA TTGCAGCACT GGGGCCAGAT GGTAAGCCCT CCCGTATCGT AGTTATCTAC
781 ACGACGGGGA GTCAGGCAAC TATGGATGAA CGAAATAGAC AGATCGCTGA GATAGGTGCC
841 TCACTGATTA AGCATTGGTA A SEQ ID NO: 5 (nucleotide sequence encoding TEM-1(S68stop))
  1 ATGAGTATTC AACATTTCCG TGTCGCCCTT ATTCCCTTTT TTGCGGCATT TTGCCTTCCT
 61 GTTTTTGCTC ACCCAGAAAC GCTGGTGAAA GTAAAAGATG CTGAAGATCA GTTGGGTGCA
121 CGAGTGGGTT ACATCGAACT GGATCTCAAC AGCGGTAAGA TCCTTGAGAG TTTTCGCCCC
181 GAAGAACGTT TTCCAATGAT GTGAACTTTT AAAGTTCTGC TATGTGGCGC GGTATTATCC
241 CGTATTGACG CCGGGCAAGA GCAACTCGGT CGCCGCATAC ACTATTCTCA GAATGACTTG
301 GTTGAGTACT CACCAGTCAC AGAAAAGCAT CTTACGGATG GCATGACAGT AAGAGAATTA
361 TGCAGTGCTG CCATAACCAT GAGTGATAAC ACTGCGGCCA ACTTACTTCT GACAACGATC
421 GGAGGACCGA AGGAGCTAAC CGCTTTTTTG CACAACATGG GGGATCATGT AACTCGCCTT
481 GATCGTTGGG AACCGGAGCT GAATGAAGCC ATACCAAACG ACGAGCGTGA CACCACGATG
541 CCTGTAGCAA TGGCAACAAC GTTGCGCAAA CTATTAACTG GCGAACTACT TACTCTAGCT
601 TCCCGGCAAC AATTAATAGA CTGGATGGAG GCGGATAAAG TTGCAGGACC ACTTCTGCGC
661 TCGGCCCTTC CGGCTGGCTG GTTTATTGCT GATAAATCTG GAGCCGGTGA GCGTGGGTCT
721 CGCGGTATCA TTGCAGCACT GGGGCCAGAT GGTAAGCCCT CCCGTATCGT AGTTATCTAC
781 ACGACGGGGA GTCAGGCAAC TATGGATGAA CGAAATAGAC AGATCGCTGA GATAGGTGCC
841 TCACTGATTA AGCATTGGTA A SEQ ID NO: 6 (nucleotide sequence encoding TEM-1(S68N))
  1 ATGAGTATTC AACATTTCCG TGTCGCCCTT ATTCCCTTTT TTGCGGCATT TTGCCTTCCT
 61 GTTTTTGCTC ACCCAGAAAC GCTGGTGAAA GTAAAAGATG CTGAAGATCA GTTGGGTGCA
121 CGAGTGGGTT ACATCGAACT GGATCTCAAC AGCGGTAAGA TCCTTGAGAG TTTTCGCCCC
181 GAAGAACGTT TTCCAATGAT GAACACTTTT AAAGTTCTGC TATGTGGCGC GGTATTATCC
241 CGTATTGACG CCGGGCAAGA GCAACTCGGT CGCCGCATAC ACTATTCTCA GAATGACTTG
301 GTTGAGTACT CACCAGTCAC AGAAAAGCAT CTTACGGATG GCATGACAGT AAGAGAATTA
361 TGCAGTGCTG CCATAACCAT GAGTGATAAC ACTGCGGCCA ACTTACTTCT GACAACGATC
421 GGAGGACCGA AGGAGCTAAC CGCTTTTTTG CACAACATGG GGGATCATGT AACTCGCCTT
481 GATCGTTGGG AACCGGAGCT GAATGAAGCC ATACCAAACG ACGAGCGTGA CACCACGATG
541 CCTGTAGCAA TGGCAACAAC GTTGCGCAAA CTATTAACTG GCGAACTACT TACTCTAGCT
601 TCCCGGCAAC AATTAATAGA CTGGATGGAG GCGGATAAAG TTGCAGGACC ACTTCTGCGC
```

TABLE 1-continued

```
661 TCGGCCCTTC CGGCTGGCTG GTTTATTGCT GATAAATCTG GAGCCGGTGA GCGTGGGTCT
721 CGCGGTATCA TTGCAGCACT GGGGCCAGAT GGTAAGCCCT CCCGTATCGT AGTTATCTAC
781 ACGACGGGGA GTCAGGCAAC TATGGATGAA CGAAATAGAC AGATCGCTGA GATAGGTGCC
841 TCACTGATTA AGCATTGGTA A

SEQ ID NO: 7 (nucleotide sequence encoding TEM-1(S68R2))
  1 ATGAGTATTC AACATTTCCG TGTCGCCCTT ATTCCCTTTT TTGCGGCATT TTGCCTTCCT
 61 GTTTTTGCTC ACCCAGAAAC GCTGGTGAAA GTAAAAGATG CTGAAGATCA GTTGGGTGCA
121 CGAGTGGGTT ACATCGAACT GGATCTCAAC AGCGGTAAGA TCCTTGAGAG TTTTCGCCCC
181 GAAGAACGTT TTCCAATGAT GCGCACTTTT AAAGTTCTGC TATGTGGCGC GGTATTATCC
241 CGTATTGACG CCGGGCAAGA GCAACTCGGT CGCCGCATAC ACTATTCTCA GAATGACTTG
301 GTTGAGTACT CACCAGTCAC AGAAAAGCAT CTTACGGATG GCATGACAGT AAGAGAATTA
361 TGCAGTGCTG CCATAACCAT GAGTGATAAC ACTGCGGCCA ACTTACTTCT GACAACGATC
421 GGAGGACCGA AGGAGCTAAC CGCTTTTTTG CACAACATGG GGGATCATGT AACTCGCCTT
481 GATCGTTGGG AACCGGAGCT GAATGAAGCC ATACCAAACG ACGAGCGTGA CACCACGATG
541 CCTGTAGCAA TGGCAACAAC GTTGCGCAAA CTATTAACTG GCGAACTACT TACTCTAGCT
601 TCCCGGCAAC AATTAATAGA CTGGATGGAG GCGGATAAAG TTGCAGGACC ACTTCTGCGC
661 TCGGCCCTTC CGGCTGGCTG GTTTATTGCT GATAAATCTG GAGCCGGTGA GCGTGGGTCT
721 CGCGGTATCA TTGCAGCACT GGGGCCAGAT GGTAAGCCCT CCCGTATCGT AGTTATCTAC
781 ACGACGGGGA GTCAGGCAAC TATGGATGAA CGAAATAGAC AGATCGCTGA GATAGGTGCC
841 TCACTGATTA AGCATTGGTA A SEQ ID NO: 8 (protein sequence of wild-type TEM-1)
  1 MSIQHFRVAL IPFFAAFCLP VFAHPETLVK VKDAEDQLGA RVGYIELDLN SGKILESFRP
 61 EERFPMMSTF KVLLCGAVLS RIDAGQEQLG RRIHYSQNDL VEYSPVTEKH LTDGMTVREL
121 CSAAITMSDN TAANLLLTTI GGPKELTAFL HNMGDHVTRL DRWEPELNEA IPNDERDTTM
181 PVAMATTLRK LLTGELLTLA SRQQLIDWME ADKVAGPLLR SALPAGWFIA DKSGAGERGS
241 RGIIAALGPD GKPSRIVVIY TTGSQATMDE RNRQIAEIGA SLIKHW
```

(bold nucleotides in SEQ ID NOS: 1-7 correspond to the codon coding for the amino acid at position 68)

The six TEM-1 constructs with mutations at S68 codon (SEQ ID NOS: 2-7) detect the following mutations: SEQ ID NO: 2 (TEM-1 (S68P)) detects C:G→T:A mutations; SEQ ID NO: 3 (TEM-1 (S68T)) detects A:T→T:A mutations; SEQ ID NO: 4 (TEM-1 (S68R1)) detects A:T→C:G and A:T→T:A mutations; SEQ ID NO: 5 (TEM-1 (S68stop)) detects G:C→C:G mutations; SEQ ID NO: 6 (TEM-1 (S68N)) detects A:T→G:C mutations; and SEQ ID NO: 7 (TEM-1 (S68R2)) detects C:G→A:T mutations.

The sequences of the oligonucleotide primers used to introduce the nucleotide mutations at the S68 position of TEM-1 are shown in Table 2.

TABLE 2

| Mutation | Forward Primer | $T_M$ | Reverse Primer | $T_M$ |
|---|---|---|---|---|
| S68P | TTTCCAAT GATGCCAAC TTTTAAAGTT (SEQ ID NO: 13) | 54.6° C. | ACTCACGT TAAGGGATT TTGGTCATGA (SEQ ID NO: 14) | 58.3° C. |
| S68T | TTCCAATG ATGACAAC TTTTAAAGT (SEQ ID NO: 15) | 51.6° C. | ACTCACGT TAAGGGATT TTGGTCATGA (SEQ ID NO: 16) | 58.3° C. |
| S68R1 | CCAATGAT GAGAACT TTTAAA (SEQ ID NO: 17) | 46.3° C. | ACTCACGT TAAGGGATT TTGGTCATGA (SEQ ID NO: 18) | 58.3° C. |
| S68stop | TTCCAATG ATGTGAAC TTTTAAAGT (SEQ ID NO: 19) | 51.6° C. | ACTCACGT TAAGGGATT TTGGTCATGA (SEQ ID NO: 20) | 58.3° C. |
| S68N | CCAATGAT GAACACTTT TAAA (SEQ ID NO: 21) | 46.8° C. | ACTCACGT TAAGGGATT TTGGTCATGA (SEQ ID NO: 22) | 58.3° C. |
| S68R2 | CCAATGAT GCGCACTTT TAAA (SEQ ID NO: 23) | 52.2° C. | ACTCACGT TAAGGGATT TTGGTCATGA (SEQ ID NO: 24) | 58.3° C. |
| Q183R | GCAGACCA TTATCGACA AAATACTCCA (SEQ ID NO: 25) | 57.0° C. | CGGAAATG TTGAATACTC ATACTCTTCCT (SEQ ID NO: 26) | 56.5° C. |

(bold nucleotides correspond to the codon coding for the amino acid at position 68)

TEMrev-GFP

Figure 1A:
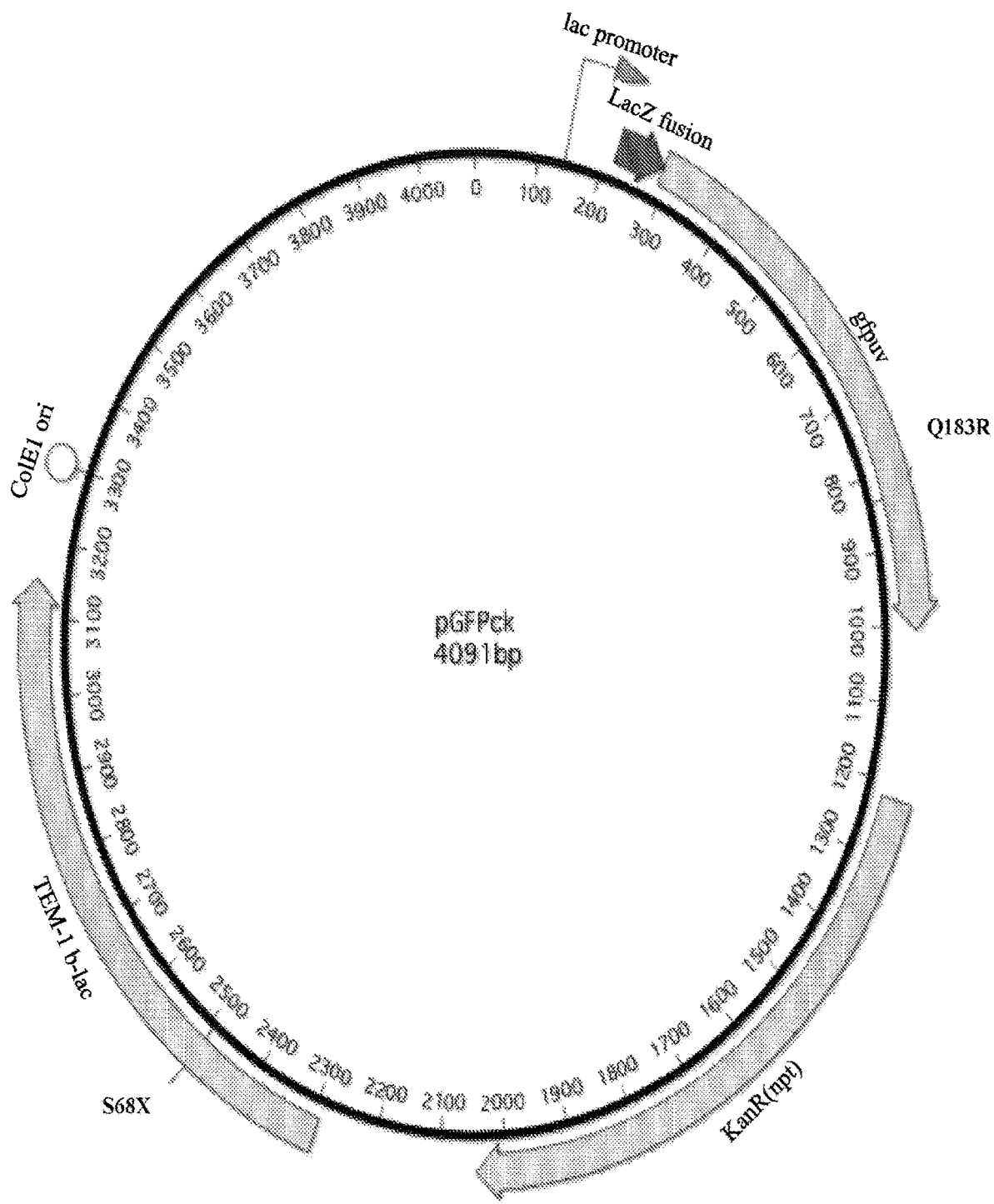
FIGS. 1A-1C: Reporter constructs. (A) TEMrev-GFP reporter. Main features: Lac promoter: 143-172; Lacz fusion: 217-288; Cycle 3 GFP: 289-1005; kanamycin resistance: 1219-2004; β-lactamase: 2291-3151 (2492-2494 S68); ColE1 plasmid origin of replication 3299-4091. In the TEMrev-GFPrev variant, the Q183R mutant codon is at positions 835-837. The mutant codon is CGA (R), which requires a G→A transition to revert back to CAA (Q). (B) sfGFPrev-TEM reporter. Main features: Ori 3999-479; sfGFP lac promoter 143-172; lacZ fusion 223-259, sfGF-Prev: 201-1014; 12 amino acid serine/glycine-rich linker 1015-1050; lactamase 1051-1911; M13 ori 1953-2462.

The TEMrev-GFP reversion reporter comprises a TEM-1 gene (e.g., SEQ ID NO: 1) or a mutant thereof (e.g., any one of SEQ ID NOS: 2-7) positioned 5' to a GFP or a GFP derivative in an expression plasmid. In some embodiments, a linker may be placed between the TEM-1 and the GFP. Examples of linkers are described in detail further herein. One example of a GFP derivative is Cycle 3 GFP, a variant of GFP optimized for fluorescence in *E. coli*. Other fluorescent proteins that may be used in the reporters and methods of the disclosure are described in detail further herein. The TEM-1 gene (e.g., SEQ ID NO: 1) or the mutant thereof (e.g., any one of SEQ ID NOS: 2-7) may be placed in the same plasmid and co-transcribed with the GFP or GFP derivative (FIG. 1A) under the control of the same promoter or two different promoters. Using this system, once an inactivated TEM-1 (e.g., an inactivated TEM-1 encoded by any one of SEQ ID NOS: 2-7) is reverted back to the active TEM-1 (e.g., wild-type TEM-1 encoded by SEQ ID NO: 1), growth in the presence of carbenicillin can be quantitatively detected using fluorescence, which has a much wider dynamic range than turbidity, without the need for lysing the cells. As a result, this construct allows the monitoring of growth over time.

sfGFPrev-TEM

Figure 1B:
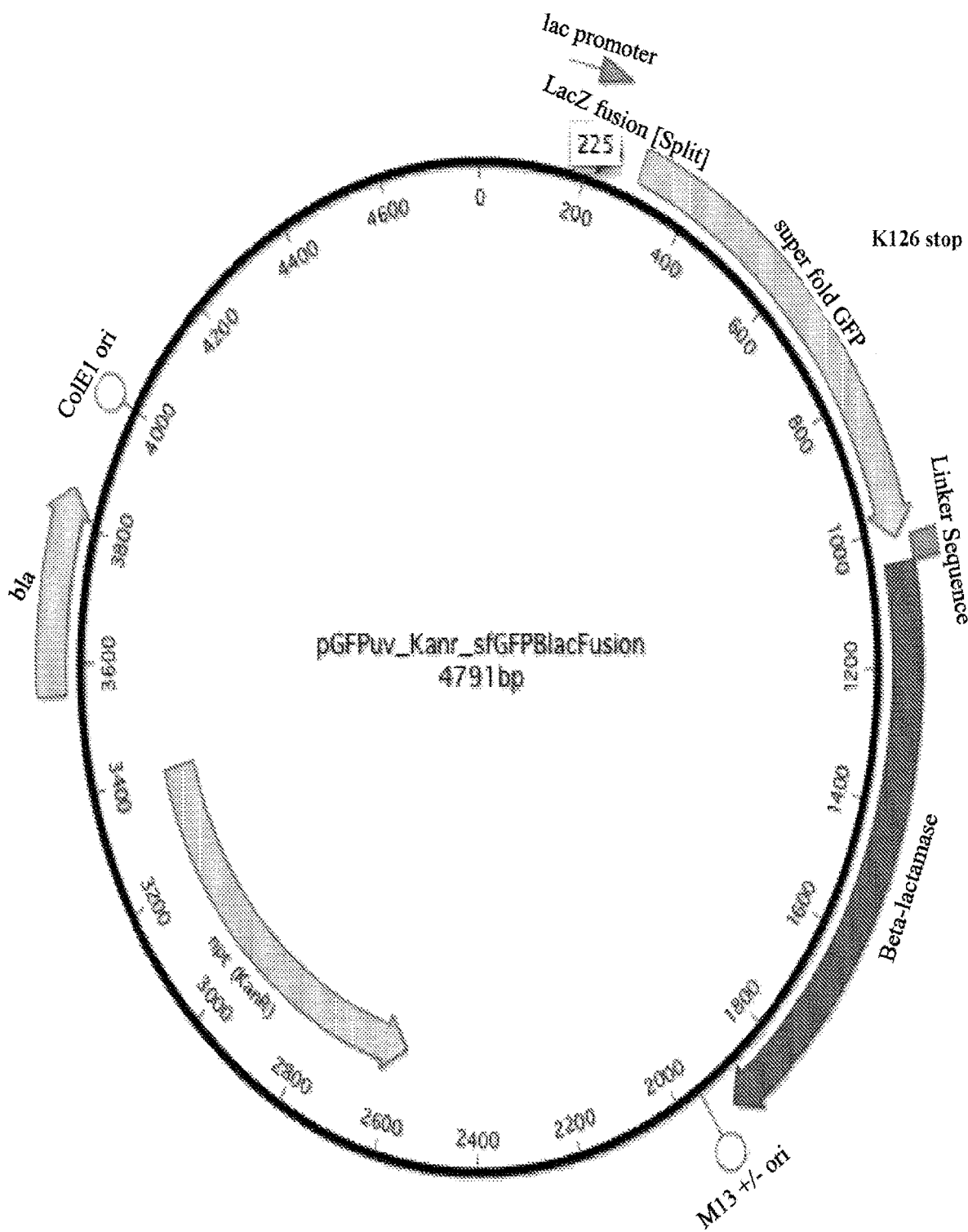

The sfGFPrev-TEM reporter comprises an inactivated GFP derivative (superfold GFP (sfGFP)) and a TEM-1 (e.g., SEQ ID NO: 1). The inactivated GFP derivative (sfGFPrev) comprises a stop codon in the GFP, rending it non-fluorescent. In some embodiments, a linker may be placed between the sfGFPrev and TEM-1 (e.g., a 12-amino acid serine and glycine-rich linker) (FIG. 1B). SEQ ID NO: 12 below shows the sequence of sfGFP-TEM fusion protein, in which sfGFP does not contain a stop codon. Q at position 69, K at position 113, and K at position 126 of SEQ ID NO: 12 may be mutated to a stop codon to create sfGFPrev-TEM reporter, in which sfGFPrev contains a stop codon.

reversion. This double set of markers allows the detection of sequential hits, separating beyond double mutation events in time and facilitating the detection of changes in mutation rates over time. The TEM-1 and the GFP may be included in the same plasmid and their expression can be driven by the same or different promoters. In some embodiments, a linker may be placed between the TEM-1 and the GFP. An example of a method of using the reporter is shown schematically in FIGS. 2A and 2B. Colonies containing the plasmid are plated on carbenicillin plates to identify reversion events in TEM-1 (i.e., a mutant TEM-1 that is inactive (any one of SEQ ID NOS: 2-7) being reverted back to the wild-type and active TEM-1 (SEQ ID NO: 1)). Non-fluorescent colonies (i.e., the colonies containing wild-type and active TEM-1 and inactivated GFP) are picked and grown in liquid culture. The plasmid DNA from these cultures is recovered and retransformed into a readout strain (e.g.,

```
SEQ ID NO: 12 (squiggly: sfGFP (SEQ ID NO: 10); bold: linker;
underlined: TEM-1)
MSKGEELFTGVVPILVELDGDVNGHKFSVRGEGEGDATNGKLTLKFICTTGKLPVPW

PTLVTTLTYGVQCFSRYPDHMKRHDFFKSAMPEGYVQERTISFKDDGTYKTRAEVK

FEGDTLVNRIELKGIDFKEDGNILGHKLEYNFNSHNVYITADKQKNGIKANFKIRHNV

EDGSVQLADHYQQNTPIGDGPVLLPDNHYLSTQSVLSKDPNEKRDHMVLLEFVTAA

GITHGMDELYKGSAGSAAGSGEFMSIQHFRVALIPFFAAFCLPVFAHPETLVKVKDAED

QLGARVGYIELDLNSGKILESFRPEERFPMMSTFKVLLCGAVLSRIDAGQEQLGRRIHYSQN

DLVEYSPVTEKHLTDGMTVRELCSAAITMSDNTAANLLLTTIGGPKELTAFLHNMGDHVTRL

DRWEPELNEAIPNDERDTTMPVAMATTLRKLLTGELLTLASRQQLIDWMEADKVAGPLLRSA

LPAGWFIADKSGAGERGSRGIIAALGPDGKPSRIVVIYTTGSQATMDERNRQIAEIGASLIK

HW
```

Superfolder GFP (sfGFP) is a derivative of Cycle 3 GFP that includes two additional mutations selected for robustness to translational fusions. sfGFPrev is preferably located at the N-terminus of TEM-1 and is preferably expressed in Top10 cells rather than JS200, AB 1157, or GW7101. The introduction of a stop codon truncating GFP expression inactivates both GFP and TEM-1, since TEM-1 is placed downstream of sfGFP, resulting in a non-fluorescent, carbenicillin-sensitive phenotype. A TGA stop codon may be introduced into sfGFP at three different positions: Q69, K113, and K126 (see SEQ ID NO: 10). Reversion of the stop codon in the mutated sfGFP back to the codon encoding the original amino acid at the particular position (e.g., Q at position 69, K at position 113, and K at position 126 of SEQ ID NO: 10) may result in fluorescence and successful translation of the entire sfGFPrev-TEM reporter. Thus, the translated and functional TEM-1 may be able to provide carbenicillin resistance to the cells.

TEMrev-GFPrev

The TEMrev-GFPrev reporter monitors mutagenesis in mutator strains quantitatively. TEMrev-GFPrev comprises a Cycle 3 GFP inactivated via a Q183R (CAA to CGA) mutation, which reverts to functional Cycle 3 GFP in response to a C:G→T:A mutation, and a TEM-1 mutant (e.g., any one of SEQ ID NOS: 2-7). Thus, this reporter couples two reversion assays: TEM-1 reversion and GFP Top10 or DH5α) to identify reversion events in GFP (e.g., non-fluorescent and inactivated GFP containing R at position 183 being reverted back to the fluorescent and active GFP containing Q at position 183) (FIG. 2B). Under these conditions, fluorescent colonies are likely to be the result of a reversion event that occurred after carbenicillin reversion, unless the reversion was already present in one of the copies of the plasmid pool when the first mutation occurred. This alternate explanation can be ruled out if the frequency of reversion is lower than one divided by the copy number of the reporter plasmid.

The TEMrev-GFPrev reporter presents an alternative to papillation assays for the characterization of mutator strains. The main advantage is that the output in this case is quantitative rather than semi-quantitative, allowing head-to-head comparisons between different mutators and/or growth conditions. Different inactivating GFP mutations can be introduced, depending on the mutagenic profile of the mutator strain. The chromophore-containing cyclized hexapeptide (amino acids at positions 64 to 69) is a good target for an inactivating mutation with a narrow tolerance to alternative amino acids. Other possible mutations in Cycle 3 GFP are described further herein (see, e.g., Table 4).

III. Fluorescent and Non-Fluorescent Proteins

Figure 5A:
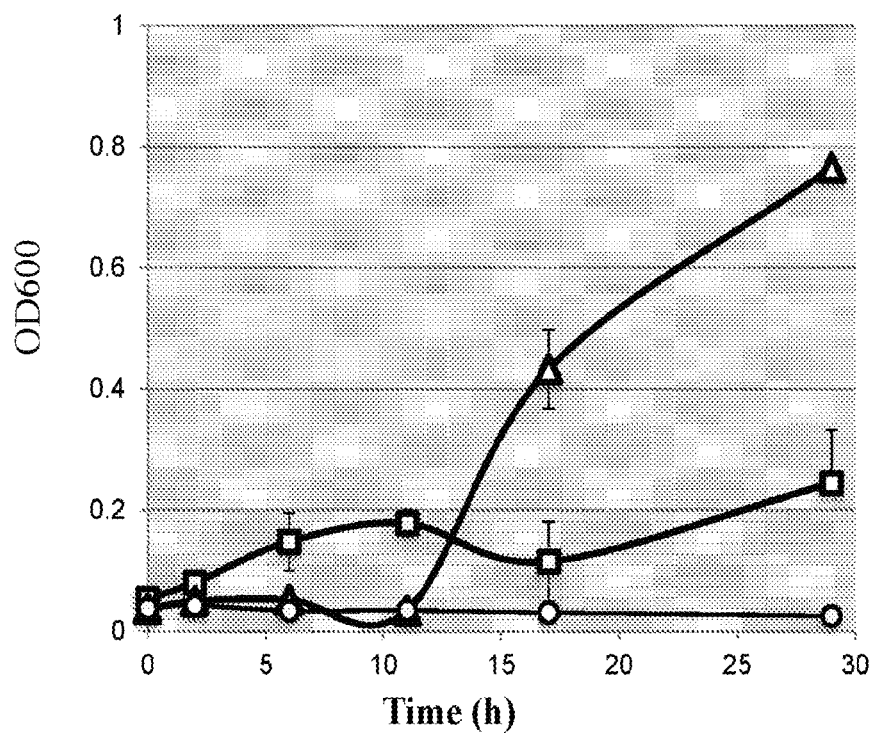
Figure 5B:
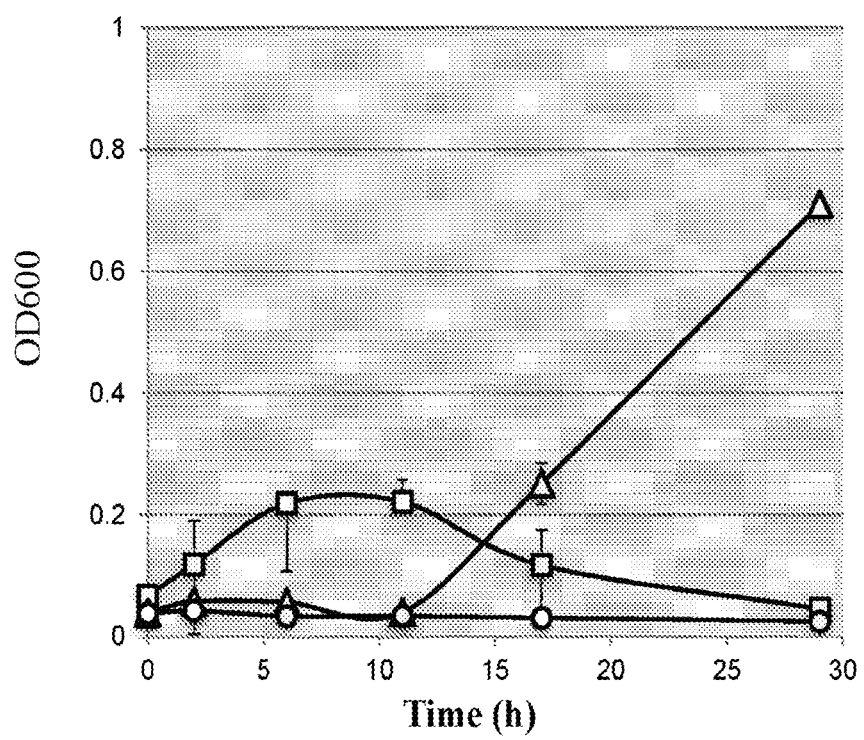
Figure 5C:
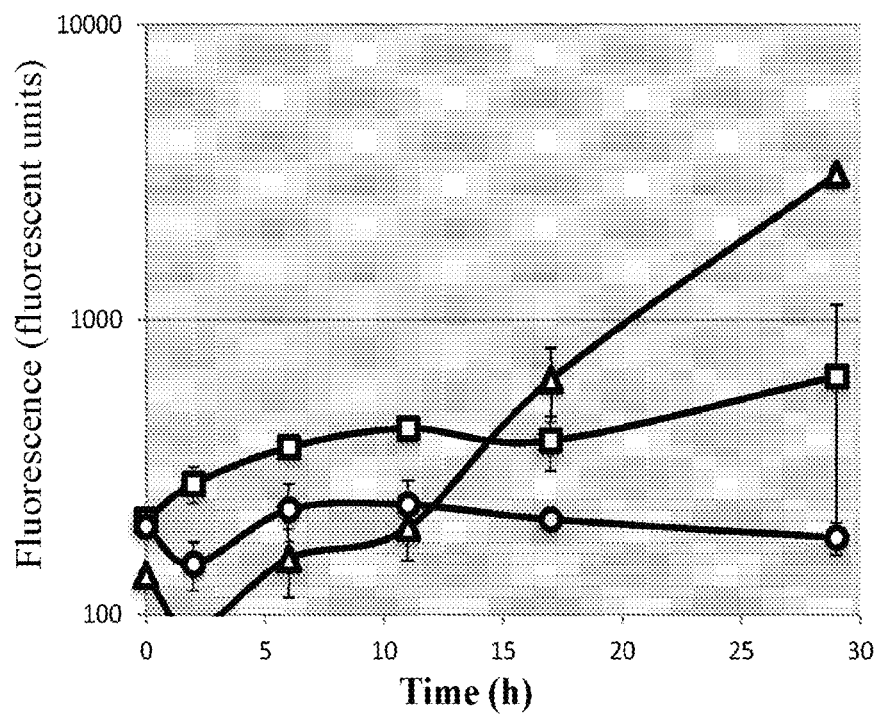
Figure 5D:
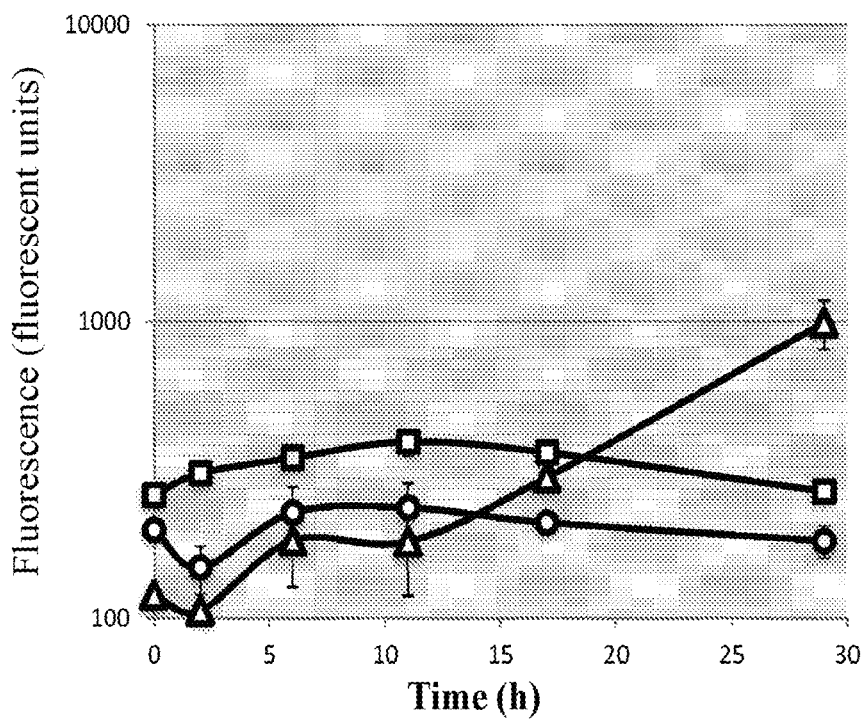

The three reporters described above (TEMrev-GFP, sfGF-Prev-TEM, and TEMrev-GFPrev) utilize a GFP or a derivative thereof in order to obtain a fluorescence readout of the reversion event. GFP facilitates quantification of growth in vivo, producing a much stronger signal than turbidity. Note that in FIGS. 5C and 5D, the results of fluorescence are shown in a logarithmic scale and that the ratio of background-to-signal is at least two orders of magnitude higher. Further, for a given time-point, the result of GFP fluorescence is quantitative. The disclosed reversion assays report that LF-Pol I produces more C:G→T:A mutations relative to A:T→C:G and A:T→T:A mutations. In FIGS. 5C and 5D, the fluorescent signal is much stronger at 30 hour time-point for the C:G→T:A reporter so a measurement at this time-point may be proportional to mutation frequency determined by plating. Relative to other quantitative reporters, GFP has several advantages that make it ideal for continuous measurement in culture: (1) it is highly stable, (2) no addition of an external substrate is necessary, (3) no cell lysis is required, and (4) it is less susceptible to substrate interference. Two levels of signal amplification are used in the disclosed methods. First, plasmids are present in multiple copies in each cell, resulting in greater total GFP expression. Second, TEM-1 revertants (cells with mutations that revert a mutant and inactive TEM-1 (e.g., a mutant TEM-1 encoded by the sequence of any one of SEQ ID NOS: 2-7) back to a wild-type and active TEM-1 (e.g., a wild-type TEM-1 encoded by the sequence of SEQ ID NO: 1)) have a growth advantage over mutant cells (i.e., cells containing a mutant and inactive TEM-1), increasing the number of cells in liquid culture at a given time in a mutator relative to a control.

The sequences of Cycle 3 GFP (SEQ ID NO: 9) and superfold GFP (sfGFP) (SEQ ID NO: 10) are shown in Table 3 below. The bold amino acids in SEQ ID NO: 9 represent the 12 amino acids each of which may be mutated to inactivate Cycle 3 GFP (Table 4 below further describes specific mutated nucleotides). The bold amino acids in SEQ ID NO: 10 (Q69, K113, and K126) are the amino acids each of which may be mutated to a stop codon (e.g., TGA) to create an inactive and truncated sfGFP.

TABLE 3

SEQ ID NO: 9 (protein sequence of Cycle 3 GFP)
MSKGEELFTGVVPILVELVDGDVNGHKFSVSGEGEGDATYGKLTLKF
ICTTGKLPVPWPTLVTTFSYGVQCFSRYPDHMKRHDFFKSAMPEGYV
QERTISFKDDGNYKTRAEVKFEGDTLVNRIELKGIDFKEDGNILGHK
LEYNYNSHNVYITADKQKNGIKANFKIRHNIEDGSVQLADHYQQNTP
IGDGPVLLPDNHYLSTQSALSKDPNEKRDHMVLLEFVTAAGITHGMD
ELYK SEQ ID NO: 10 (protein sequence of sfGFP)
MSKGEELFTGVVPILVELDGDVNGHKFSVRGEGEGDATNGKLTLKFI
CTTGKLPVPWPTLVTTLTYGVQCFSRYPDHMKRHDFFKSAMPEGYVQ
ERTISFKDDGTYKTRAEVKFEGDTLVNRIELKGIDFKEDGNILGHKL
EYNFNSHNVYITADKQKNGIKANFKIRHNVEDGSVQLADHYQQNTPI
GDGPVLLPDNHYLSTQSVLSKDPNEKRDHMVLLEFVTAAGITHGMDE
LYK Other fluorescent proteins may also be used in the reporters described herein. Examples of fluorescent proteins are well-known in the art, see, e.g., Gert-Jan Kremers et al., *J Cell Sci.* 124:157, 2011 and Stepanenko et al., *Curr Protein Pept Sci.* 9:338, 2008. Examples of fluorescent proteins include, but are not limited to, green fluorescent protein (GFP), yellow fluorescent protein (YFP), enhanced blue fluorescent protein (EBFP), azurite, GFPuv, T-Sapphire, Cerulean, mCFP, mTurquoise2, ECFP, CyPet, mKeima-Red, TagCFP, AmCyan1, mTFP1, Midoriishi Cyan, TurboGFP, TagGFP, Emerald, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2, mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry.

To create an inactive or non-fluorescent version of a fluorescent protein, in some embodiments, a stop codon may be introduced within the protein sequence. For example, the bold amino acids in SEQ ID NO: 10 (Q69, K113, and K126) indicate the amino acids each of which may be mutated to a stop codon (e.g., TGA) to create an inactive and truncated sfGFP. Table 4 further lists the potential mutants and the mutated nucleotide that may be introduced into Cycle 3 GFP to create a non-fluorescent Cycle 3 GFP. A sequence of a non-fluorescent Cycle 3 GFP is shown in SEQ ID NO: 11, wherein Q at position 183 of SEQ ID NO: 9 is mutated to an R. Further, as described above, one or more amino acids within the chromophore-containing cyclized hexapeptide of a fluorescent protein (i.e., amino acids at positions 64 to 69) may be mutated to produce a non-fluorescent protein. One of skill in the art would have the ability and knowledge to identify amino acids within the chromophore of a fluorescent protein, see, e.g., Stepanenko et al., *Biotechniques* 51(5): 313, 2011, Sarkisyan et al., *Sci Reports* 2:608, 2012, and Gross et al., *Proc Natl Acad Sci USA.* 97(22): 11990-11995, 2000.

SEQ ID NO: 11 (Cycle 3 GFP (Q183R)):
MSKGEELFTGVVPILVELDGDVNGHKFSVSGEGEGDATYGKLTLKFICTT

GKLPVPWPTLVTTFSYGVQCFSRYPDHMKRHDFFKSAMPEGYVQERTISF

KDDGNYKTRAEVKFEGDTLVNRIELKGIDFKEDGNILGHKLEYNYNSHNV

YITADKQKNGIKANFKIRHNIEDGSVQLADHYRQNTPIGDGPVLLPDNHY

LSTQSALSKDPNEKRDHMVLLEFVTAAGITHGMDELYK

TABLE 4

| Amino acid position of SEQ ID NO: 9 | Nucleotide substitution | Original Codon | Original amino acid | Mutant amino acid |
|---|---|---|---|---|
| 48 | G to A | TGC | C | Y |
| 49 | A to G | ACT | T | A |
| 56 | C to T | CCA | P | L |
| 61 | T to A | GTC | V | D |
| 62 | A to G | ACT | T | A |
| 89 | C to T | CCC | P | S |
| 91 | G to A | GGT | G | D |
| 92 | A to G | TAT | Y | C |
| 103 | A to T | GAC | D | V |
| 143 | A to G | TAC | Y | C |
| 183 | A to C | CAA | Q | H |
| 213 | A to G | GAA | E | G |

In some embodiments, a reporter may contain a mutant TEM-1 (e.g., the sequence of any one of SEQ ID NOS: 2-7)

joined to the N-terminus of a fluorescent protein (similar to the TEMrev-GFP reporter described above). A reporter may also contain a mutant and inactive fluorescent protein joined to the N-terminus of a wild-type TEM-1 (e.g., the sequence of SEQ ID NO: 1) (similar to the sfGFPrev-TEM reporter described above). In some embodiments, a reporter may contain a mutant TEM-1 (e.g., the sequence of any one of SEQ ID NOS: 2-7) joined to the N-terminus or C-terminus of a mutant and inactive fluorescent protein (similar to the TEMrev-GFPrev reporter described above). In any of the reporters described herein, a linker may be optionally placed between the TEM-1 or a mutant thereof and the active or inactive fluorescent protein. Examples of linkers are described in detail further herein.

IV. Linkers

In some embodiments, a linker may be used as a linkage or connection between a TEM-1 or a mutant thereof and an active or inactive fluorescent protein. The linker may be a peptide including, e.g., 3-200 amino acids (e.g., 3-200, 3-180, 3-160, 3-140, 3-120, 3-100, 3-90, 3-80, 3-70, 3-60, 3-50, 3-45, 3-40, 3-35, 3-30, 3-25, 3-20, 3-15, 3-10, 3-9, 3-8, 3-7, 3-6, 3-5, 3-4, 4-200, 5-200, 6-200, 7-200, 8-200, 9-200, 10-200, 15-200, 20-200, 25-200, 30-200, 35-200, 40-200, 45-200, 50-200, 60-200, 70-200, 80-200, 90-200, 100-200, 120-200, 140-200, 160-200, or 180-200 amino acids). In some embodiments, a linker may be a peptide including 8-16 amino acids (e.g., 8, 9, 10, 11, 12, 13, 14, 15, or 15 amino acids). Suitable linkers are known in the art, and include, for example, peptide linkers containing flexible amino acid residues such as glycine and serine. In certain embodiments, a linker can contain motifs, e.g., multiple or repeating motifs, of GS, GGS, GGGGS (SEQ ID NO: 27), GGSG (SEQ ID NO: 28), or SGGG (SEQ ID NO: 29). In certain embodiments, a linker can contain 2 to 12 amino acids including motifs of GS, e.g., GS, GSGS (SEQ ID NO: 30), GSGSGS (SEQ ID NO: 31), GSGSGSGS (SEQ ID NO: 32), GSGSGSGSGS (SEQ ID NO: 33), or GSGSGSGSGSGS (SEQ ID NO: 34). In certain other embodiments, a linker can contain 3 to 12 amino acids including motifs of GGS, e.g., GGS, GGSGGS (SEQ ID NO: 35), GGSGGSGGS (SEQ ID NO: 36), and GGSGGSGGSGGS (SEQ ID NO: 37). In yet other embodiments, a linker can contain 4 to 20 amino acids including motifs of GGSG (SEQ ID NO: 28), e.g., GGSGGGSG (SEQ ID NO: 38), GGSGGGSGGGSG (SEQ ID NO: 39), GGSGGGSGGGSGGGSG (SEQ ID NO: 40), or GGSGGGSGGGSGGGSGGGSG (SEQ ID NO: 41). In other embodiments, a linker can contain motifs of GGGGS (SEQ ID NO: 27), e.g., GGGGSGGGGS (SEQ ID NO: 42) or GGGGSGGGGSGGGGS (SEQ ID NO: 43).

In other embodiments, a linker can also contain amino acids other than glycine and serine, e.g., GSAGSAAGSGEF (SEQ ID NO: 44), GENLYFQSGG (SEQ ID NO: 45), or SACYCELS (SEQ ID NO: 46). In particular embodiments, the linker is GSAGSAAGSGEF (SEQ ID NO: 44).

EXAMPLES

Example 1—Brief Description of Experimental Protocol

Materials
  Transformation and Mutagenesis
  Competent cells: Top10, JS200-pHSG_WTPolA, and JS200-pHSG_EP1 PolA
  ColE1 vectors: pGFPck (Cycle 3; fluorescent), pGFPck (Q183R; non-fluorescent), sfGFP, and pGFPuv_KanR
  Other materials: 500 mL centrifuge bottles, Eppendorf centrifuge 5810 R (Eppendorf), 50 mL conical tubes (Fisher Scientific, Cat.#1443222), 15 mL culture tubes (E&K Scientific, Cat.# EK-62262), LB broth (Fisher Scientific, Cat.# BP1426-2), LB agar (Fisher Scientific, Cat.# BP1425-2), 100 mm×15 mm disposable Petri dishes (Fisher Scientific, Cat.# FB0875713), kanamycin solution (30 mg/mL, store at −20° C.), kanamycin (30 µg/mL) LB agar and broth, 1.5 mL microfuge tubes (E&K Scientific, Cat.#280150), Tropi-Cooler, Model 260014 (Boekel Scientific), MaxQ 4000 shaker/incubator (Barnstead International), and water-jacketed incubator (Forma Scientific)

Washing Plates
  Materials: kanamycin (30 µg/mL) LB broth, plate spinner, plate spreader, ethanol (200 proof), Bunsen burner, spectrophotometer cuvettes (Fisher Scientific, Cat.#14955127), 1.5 mL microfuge tubes (E&K Scientific, Cat.#280150), and BioMate 3 Spectrophotometer (Thermo Scientific)

Readout (Plates)
  Materials: kanamycin (30 µg/mL) LB agar and broth, carbenicillin (100 pg/mL) LB agar and broth, 1.5 mL microfuge tubes (E&K Scientific, Cat.#280150), plate spreader, plate spinner, ethanol (200 proof), Bunsen burner, water-jacketed incubator (Forma Scientific), and UV Light Readout (Liquid Culture Assay)
  Materials: kanamycin (30 µg/mL) LB broth, carbenicillin (100 µg/mL) LB broth, 3 mm diameter glass beads (Sigma-Aldrich, Cat.# Z265926), AirPore tape sheets (Qiagen, Cat.#2017-10-RP), 96-well round-bottomed deep-well plates (Fisher Scientific, Cat.#10011-944), 96-well flat-bottomed black-walled plates (Fisher Scientific, Cat.#82050-744), microtiter plate lids (Fisher Scientific, Cat.#82050-829), MaxQ 4000 shaker/incubator (Barnstead International), SpectraMax M2e Fluorometric and Spectrophotometric plate reader, dual monochromators, and Absorbance 200-1000 nm and excitation 250-850 nm (Molecular Devices)

Plasmid Recovery
  Materials 15 mL culture tubes (E&K Scientific, Cat.# EK-62262), 1.5 mL microfuge tubes (E&K Scientific, Cat.#280150), and Nucleospin Plasmid (NoLid) kit (Macherey-Nagel, Cat.#740499.250)

Sequencing Plasmids of Interest
  NanoDrop ND-1000 Spectrophotometer for DNA quantification (Thermo Scientific), 0.6 mL microfuge tubes (E&K Scientific, Cat.#280060-S), and MacVector version 12.7.5 for sequence analysis (MacVector Inc.)

Methods
  Transformation of ColE1 Plasmids by Heat-Shock Method
  Prepare a 5 mL overnight culture in a 15 mL culture tube in LB media for the cell line of interest. If necessary, include selective antibiotic in the media for the desired cell line. Expand this culture into a sterile 1 L Erlenmeyer flask containing 500 mL of LB media with selective antibiotic. Incubate this flask at 30° C. or 37° C. (depending on the cell line; incubate JS200 cell lines at 30° C., and all others at 37° C.) with shaking (225 rpm) until exponential phase is reached ($OD_{600}$=0.4-0.6). Chill the flask containing the cells on ice for 20 minutes. For best results, cells should be kept chilled at all times. Transfer the liquid cultures to 500 mL plastic centrifuge bottles and centrifuge at 4000 rpm for 20 minutes at 4° C. Pour off supernatant, and resuspend the cell pellet in 50 mL of chilled calcium chloride solution (100 mM $CaCl_2$, 10 mM HEPES, 15% Glycerol, pH 7). Transfer the resuspended cells into a 50 mL conical tube. Centrifuge the cells at 4000 rpm for 20 minutes at 4° C. Pour off supernatant, and resuspend the cell pellet in 50 mL of chilled calcium chloride solution, and centrifuge the cells at 4000 rpm for 20 minutes at 4° C. (repeat 3 times).

After third wash with calcium chloride solution, pour off supernatant, and resuspend the cells in 5 mL of chilled calcium chloride solution. Keep cells on wet ice and use immediately, or aliquot into 1.5 mL microfuge tubes and place on dry ice for storage at −80° C. Pipette 40 μL of cells into 1.5 mL microfuge tube per transformation. Pipette 100 μg of plasmid DNA into the tube containing the competent cells and mix well by pipetting up and down. Incubate on ice for 30 minutes. Heat-shock the cells at 42° C. for 90 seconds on Tropicooler block. Place cells back on ice for 5 minutes. Add 1 mL of LB Broth to the microfuge tube containing the cells and DNA. Allow the cells to recover for 30 minutes to 1 hour at 30° C. or 37° C. (depending on the cell line; incubate JS200 cell lines at 30° C., and all others at 37° C.) with shaking (225 rpm). Plate transformed cells by spreading 100 μL with sterile plate spreader onto pre-warmed LB agar plates containing 30 μg/mL kanamycin. Allow the cells to grow overnight at either 30° C. or 37° C.

Inducing Mutagenesis

For ColE1 on plasmids which have been transformed into JS200-pHSG_EP1 PolA cell strains, incubate at 37° C. to induce mutagenesis. Use the same plasmids transformed into JS200-pHSG_WTPolA as control.

Washing Plates

Observe plate for bacterial colony lawn formation, which consists of a high density of colonies. Place plate on a plate spinner. Add 1 mL LB broth containing 30 μg/mL kanamycin directly to the plate surface containing bacterial growth. Use sterile plate spreader to collect colonies into LB Broth. Tilt plate slightly of collect broth containing harvested colonies into one area, and transfer as much as possible into a 1.5 mL microfuge tube. Repeat colony harvesting steps again. Collect second wash into the same 1.5 mL microfuge tube. Dilute plate washes 1:20 directly in spectrophotometer cuvettes (950 μL media+50 μL plate wash), and mix by pipetting. Measure $OD_{600}$ of diluted plate wash using the BioMate 3 spectrophotometer, and multiply the measurement by 20 to obtain the actual $OD_{600}$ of the undiluted plate wash. Normalize all plate washes to $OD_{600}=1$ prior to readout experiments.

Readout (Plates)

Pre-warm LB agar plates containing 30 rig/mL kanamycin and LB agar plates containing 100 μg/mL carbenicillin in incubator set at 30° C. or 37° C. (depending on the cell line; incubate JS200 cell lines at 30° C., and all others at 37° C.). Plate 100 μL of plate washes to pre-warmed plates (all washes plated to both LB agar plates containing 30 μg/mL kanamycin and LB agar plates containing 100 μg/mL carbenicillin) at appropriate dilutions to yield countable colonies. Incubate at 30° C. or 37° C. (depending on the cell line; incubate JS200 cell lines at 30° C., and all others at 37° C.) overnight. Determine the number of colonies on each plate. Use counts to determine CFU/mL of OD normalized cultures on each type of selective media.

Determine percent of TEM β-lactamase S68 revertants by the formula:

% Reversion=[(CFU/mL(carbenicillin))/(CFU/mL (kanamycin))]*100

Readout (Liquid Culture Assay)

Aseptically place one sterile 3 mm diameter glass bead into each well of a 96-well deep-well round-bottomed plate using sterilized forceps. Transfer 950 μL of LB broth containing 30 pg/mL kanamycin to one well and 950 μL of LB broth containing 100 μg/mL carbenicillin to another well for each construct to be tested at each time point. Inoculate wells with 50 μL of 1:10 diluted plate washes (final inoculation $OD_{600}=0.05$). Cover with AirPore tape sheet. Remove 200 μL of T0 time point to 96-well black-walled clear-bottomed flat-bottomed plates, cover with sterile plate lid, place at 4° C. Cover deep-welled plate with sterile plate lid and place in incubator at 30° C. or 37° C. (depending on the cell line; incubate JS200 cell lines at 30° C., and all others at 37° C.) with shaking (325 rpm). At appropriate time points, remove 200 μL of culture from pre-assigned well to 96-well black-walled plates. Between time points, the black-walled plates should be stored at 4° C., and the deep-welled plates should be incubated at the appropriate temperature with shaking. At the last time point, remove culture and un-inoculated blank wells to black-walled plates. Read $OD_{600}$ and fluorescence (ex. 395 nm, em. 509 nm) from black-walled plates on SpectraMax M2e Fluorometric and Spectrophotometric plate reader. Plot $OD_{600}$ versus time and fluorescence versus time for constructs under both kanamycin selection and carbenicillin selection to estimate relative rates of TEM β-lactamase S68 reversion.

Plasmid Recovery

Pick reversion colonies from LB agar plates containing 100 μg/mL carbenicillin generated previously, and inoculate into 3 mL of LB broth containing 100 μg/mL carbenicillin. Grow cultures overnight at 30° C. or 37° C. (depending on the cell line; incubate JS200 cell lines at 30° C., and all others at 37° C.) with shaking (225 rpm). Harvest cells by centrifugation at 11,000×g for 1 minute, pour off supernatant, and isolate plasmid DNA (miniprep) based on manufacturer's instructions.

Sequencing Plasmids of Interest

Quantify plasmid DNA yield and purity using NanoDrop Spectrophotometer. Open NanoDrop software (ND-1000, version 3.8.1), and select nucleic acid quantification. Place 2 μL of purified water on cleaned pedestal and lower arm to initialize spectrophotometer. Place 2 μL of elution buffer on cleaned pedestal and lower arm to blank spectrophotometer. Place 2 μL of sample to be quantified on cleaned pedestal and lower arm to measure absorption spectrum between 220 nm and 350 nm. Transfer 0.5 to 1 μg of plasmid DNA to 0.6 μL microfuge tube with appropriate label. Transfer 10 μL of 5 μM sequencing primer to 0.6 μL microfuge tube with appropriate label. Send plasmid DNA and sequencing primer to sequencing facility. Assemble and analyze sequences using the program MacVector version 12.7.5.

Other Experimental Notes

Pre-warming plates prior to plating cells is essential for efficient mutagenesis. Typical recovery per 2 mL of LB is about 1.5 mL of plate wash. Experimenter must estimate dilution needed to achieve a total number of colonies on plate between 30-300. This may require some trial and error. The results indicate that a dilution factor of $10^{-7}$ is effective for all constructs and controls on kanamycin plates and positive controls (WT β-lactamase) on carbenicillin plates and no dilution for negative controls on carbenicillin plates. For reporter constructs on carbenicillin plates, dilutions may vary depending on the expected reversion frequency, but generally range between no dilution and a dilution factor of $10^{-3}$. Be sure to take note of the dilution factor used for each construct plated, as this will be used to calculate CFU/mL.

Sterilize forceps by dipping in ethanol and holding over flame until red hot. It is recommended to have replicates at each time point. Inoculate different time points and different constructs and controls into separate wells. Inoculate each culture into both kanamycin wells and carbenicillin wells. Leave at least three wells on each plate un-inoculated, to be used as blanks during spectrophotometry/fluorimetry. For cell lines growing at 30° C., culture growth will be slower. Plan time points accordingly. Take 200 µL from fresh wells at each time point. Do not resample wells that have already been sampled at previous time points. Sample well by stabbing the micropipette tip through the AirPore sheet. Use caution to avoid disturbing/cross-contaminating wells containing later time points or blanks.

Example 2—Experimental Validation

To validate the reporter system, an error-prone Pol I plasmid replication was used. This system is based on expression of an error-prone variant of DNA polymerase I (Pol I) in JS200, a polA12 (temperature-sensitive) strain of E. coli. Shift of this strain to 37° C. makes J200 cells dependent on the activity of the error-prone variant of Pol I (low fidelity Pol I or LF-Pol I) for survival. Specifically, LF-Pol I performs ColE1 plasmid replication and processes of Okazaki fragments during lagging-strand replication in both the plasmid and in chromosomal DNA. This variant bears three mutations that decrease its replication fidelity: I709N in motif A (broadening its active site), A759R in motif B (favoring its closed conformation), and D424A (inactivating its proofreading domain).

Overnight culture under restrictive conditions (37° C.) leads to an increased mutation frequency in ColE1 plasmids by over three orders of magnitude in vivo, about 1 nucleotide substitution per 1.5 kb. This is true for most of the plasmid sequence, where Pol I appears to be competing with Pol III. These loads are higher in areas replicated exclusively by Pol I: the 150 nucleotides immediately downstream of the RNA/DNA switch (leading-strand synthesis by Pol I), about 500 nucleotides upstream of the RNA/DNA switch (gap-filling of lagging-strand synthesis by Pol I), and about 20 nucleotide patches corresponding to areas of Okazaki fragment processing by Pol I. It is worth noting that LF-Pol I is partially dominant in vivo, as expression of this polymerase still produces ColE1 plasmid mutagenesis at permissive temperature or in polA WT strains, albeit with about 4 fold lower frequency relative to JS200 at restrictive temperature.

In terms of mutation spectrum, the mutation frequency of LF Pol I on a single strand in vivo was estimated. The vast majority of mutations (>95%) are point mutations and can be grouped in four groups: most frequent: C→T transitions (60%); frequent: A→G and A→T (20 and 10% of the total), respectively); rare: G→T, G→A, and G→T, and extremely rare: T→C, T→A, A→C, and C→G. The observation of the very low frequency of T→C transitions indicates that mismatch repair appears to be intact in these cells. Given that the reporter detects mutations in double-stranded DNA, i.e., in pairs of complementary mutations, the following ranking based on frequency is expected: C to T/G to A (most frequent)>A to G/T to C, A to T/T to A>G to T/C to A>T to G/A to C>G to C/C to G.

Example 3—Reversion Detection Using Six TEMrev-GFP Reporters

Figure 1C:
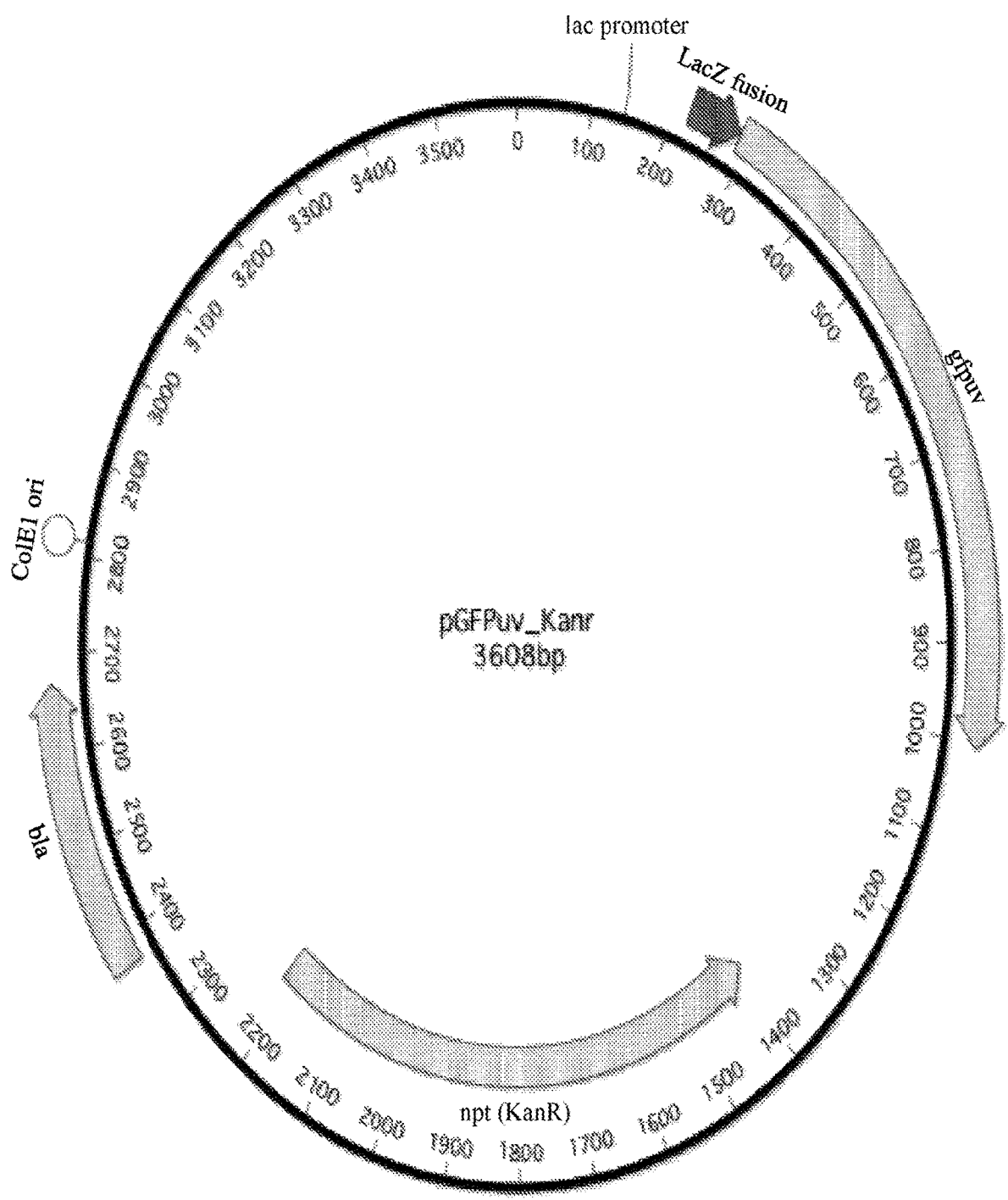

Six TEMrev-GFP reporters (e.g., each of the sequence of any one of SEQ ID NOS: 2-7 joined to the sequence of GFP), a TEM-GFP positive control, and a negative control not bearing the TEM1 gene (FIG. 1C) were transformed into JS200 E. coli cells expressing LF-Pol I. As an additional control, these plasmids were also transformed into a JS200 expressing WT Pol I. After recovery at 30° C., cells were plated onto LB agar plates pre-warmed to 37° C. containing kanamycin, thus switching the transformants to restrictive conditions. Mutagenesis occurred during growth overnight at 37° C.

For the TEMrev-GFP reporter, growth of the transformants overnight produced a high density of colonies (near-lawn). These colonies were harvested from the plate into about 1.5 ml of LB broth. Absorbance at 600 nm was determined to normalize the washes to $OD_{600}=1$. These dilutions were used to plate kanamycin plates (at further dilution of $1:10^7$) and carbenicillin plates at different dilutions, depending on reversion frequencies (between neat and $1:10^3$ dilutions). This time plates were incubated overnight at 30° C. to minimize additional mutagenesis. Following incubation, the number of colonies on each plate were counted, and this number was used to calculate the reversion rate for each reporter (FIGS. 4A and 4B). Interestingly, fluorescence was not uniform across all carbenicillin-resistant colonies, possibly due to the presence of additional mutations affecting GFP expression and/or function.

Three of the reporters produced between 10 and 100-fold higher background mutation frequencies in the control strain expressing WT Pol I relative to the other three (FIG. 4A). The three reporters with greater spontaneous mutation frequency are: S68stop (G:C→C:G), S68N (A:T→G:C), and S68R2 (C:G→A:T). Given that Pol I appears to compete with Pol III for ColE1 plasmid replication, the observed increase in spontaneous mutation frequency could be due to an increase in the fraction of plasmids that are replicated by Pol I as a result of WT Pol I overexpression. Indeed, Pol I appears to be more mutagenic than Pol III in vivo (particularly for transitions), and its fidelity can be modulated by Pols II and IV.

Two pairs exhibit lower reversion frequencies than expected: A:T→G:C and G:C→T:G. This could be the result of sequence-context dependent effects, which can be in part due to differential efficiency of mismatch repair. The observation that S68R1, which detects A:T→C:G and A:T→T:A mutations, produces fewer reversions than S68T, which detects A:T→T:A alone directly confirms the impact of local sequence context on mutation rates. Overall, then, profiling a mutation spectrum using the disclosed TEMrev-GFP reporter gives a general idea of which types of point mutations are favored, particularly if there is as strong bias for a specific type.

For the sfGFPrev-TEM reporter containing K126stop mutation in sfGFPrev, JS200 cells expressing LF-Pol I and transformed with the sfGFPrev-TEM reporter that were plated at 30° C. produced a semi-lawn of carbenicillin-resistant, fluorescent colonies. Sequencing of 10 these colonies showed point mutations at the stop codon in all cases, producing an L (three times), W (three times), Q (twice), and Y (twice). In eight of these cases, the WT signal was still detectable, suggesting that the plasmid carrying the K126 point mutation had not replaced all the copies of the original K126 stop reporter. Cells expressing WT-Pol I had practically no colonies (FIGS. 3A and 3B)

Example 4—Growth and Fluorescence Emission Kinetics

Following mutagenesis, plates were washed with LB media and normalized to $OD_{600}=1.0$ as described above. These cultures were used to inoculate 96-well plates in a 1:20 dilution. The plates were deep-well round-bottom plates with glass beads (to facilitate oxygenation) and a final volume of 1 mL was added to each well. The plates were then covered with AirPore breathable sheets, in order to protect against cross-contamination and evaporation effects, while still allowing for microbe growth under aerobic conditions. Cells were grown at 30° C. with shaking at 325 rpm. At different time-points, 200 μL of each culture was transferred to a set of black-walled flat-bottomed 96-well microtiter plates and kept at 4° C. At the end of the experiment, these plates were read on a fluorescence-enabled spectrophotometric plate reader for absorbance at 600 nm to determine growth and for fluorescence (with excitement λ=395 nm, and emission λ=509 nm). Results were then used to plot growth kinetics curves for each construct under each antibiotic selection. FIGS. 5A-5D shows the growth and fluorescence emission kinetics for two of the reporters, S68P (which detects C:G-T:A mutations; the sequence of SEQ ID NO: 2 joined to the sequence of GFP)(FIGS. 5A and 5C) and for S68R1 (which detects (A:T→C:G and A:T→T:A mutations; the sequence of SEQ ID NO: 4 joined to the sequence of GFP)(FIGS. 5B and 5D)

Example 5—Analysis of Double Reversion Events

For continuous mutagenesis detection, colonies expressing LF-Pol I and bearing the TEMrev-GFPrev reporter were plated under restrictive conditions as described above, but at a higher dilution factor in order to obtain individual carbenicilin-resistant colonies. Three non-fluorescent colonies were picked, and grown in liquid culture under restrictive conditions. The DNA from these cultures was recovered and retransformed into DH5α cells to identify R183Q (fluorescent) revertants (FIGS. 2A and 2B). A total of 11,100 colonies from these three transformations were obtained. Of these, 2 colonies in two separate transformations exhibiting bright fluorescence (one of them is shown in FIG. 6) were found. Control plasmids expressing WT Pol I produced 73,500 colonies, none of which exhibited fluorescence based on visual inspection.

A reversion frequency at the Q183R site (revert R183 back to Q183) was found to be about 1 in $10^4$ cells. This frequency is 2-3 fold lower than that observed at the TEMrev site (revert a mutant TEM-1 back to a wild-type TEM-1). It is unclear which amino acid substitutions are allowed at this site, but a C:G-T:A mutation reverts R at position 183 back to Q. Given that C:G-T:A mutations are the predominant mutations introduced by LF-Pol I, it can be assumed that this is the main mutation driving the reversion.

To control for the possibility that R183Q reversions were already present in one of the copies of the plasmid pool of the original colony, the original carbenicillin-resistant colonies were expanded under permissive conditions as well. Only 2 fluorescent colonies were observed in 9,300 transformants, and no fluorescent colonies were observed in plasmids recovered from cells expressing WT Pol I (113,000 transformants). Given that the average plasmid copy number for the reporter plasmid in LF-Pol expressing cells is less than ten plasmids per cell, these results confirm that the observed fluorescent colonies are most likely the result of mutations at the 183 position of GFP that occurred after the P68S reversion.

A reversion frequency that is far lower than 1 divided by plasmid copy number confirms that the revertants were not present in the cell where the original reversion of the TEM-1 marker occurred, and therefore argues that the GFP reversion occurred at a later time-point. This observation has two additional implications: (1) it suggests that under restrictive conditions, LF-Pol I-expressing cells continue to generate mutations after a first passage, albeit at a reduced rate relative to early culture; (2) it also suggests that at the permissive temperature, where the mutation rate is already low, mutation rates can be sustained over longer periods of time. Random mutagenesis systems that maintain mutation rates over time would greatly facilitate directed evolution. Thus, the disclosed reporter can be used to fine-tune existing mutator strains such as XL-1 red, the MP6 mutagenesis system, or strains with altered dNTP pools to identify conditions supporting constant mutation rates over time.

What is claimed is:

1. A method of detecting mutagenesis in *Escherichia coli* (*E. coli*), the method comprising:
    (a) culturing *E. coli* cells in a first liquid culture at a restrictive temperature, wherein the *E. coli* cells in the first liquid culture comprise a plasmid comprising
        (i) a first polynucleotide encoding an inactive β-lactamase and having a nucleotide sequence selected from the group consisting of SEQ ID NOS: 2-7, and
        (ii) a second polynucleotide encoding a fluorescent protein,
        wherein the first polynucleotide and the second polynucleotide are operably linked to a first promoter,
        wherein when the first and second polynucleotides are expressed as a fusion and when the fluorescent protein is green fluorescent protein (GFP), the GFP is superfolder GFP and the inactive β-lactamase is located C-terminally to the superfolder GFP in the fusion protein;
    wherein the *E. coli* cells further comprise
        (i) an error prone polymerase I operably linked to a second promoter, where the second promoter promotes transcription of the error prone polymerase I at the restrictive temperature, and
        (ii) a wild type polymerase I that is operably linked to a third promoter, wherein the third promoter promotes transcription of the error prone polymerase I at a permissive temperature;
    (b) plating the *E. coli* cells in the first liquid culture on a solid media comprising a β-lactam antibiotic;
    (c) incubating the first solid media at the permissive temperature;
    (d) selecting a fluorescent *E. coli* colony from the solid media;
    (e) culturing the fluorescent *E. coli* colony in a second liquid culture at the permissive temperature, wherein the second liquid culture comprises the β-lactam antibiotic; and
    (f) measuring a change in growth of the *E. coli* cells of the second liquid culture relative to the first liquid culture, wherein the change in growth indicates mutagenesis of the inactive β-lactamase to an active β-lactamase.

2. The method of claim 1, wherein the first polynucleotide is located 5' to the second polynucleotide in the plasmid.

3. The method of claim 1, wherein the plasmid further comprises a linker between the first polynucleotide and the second polynucleotide.

4. The method of claim 1, wherein the β-lactam antibiotic is carbenicillin.

5. The method of claim 1, wherein the β-lactamase is TEM-1.

6. The method of claim 1, wherein the fluorescent protein comprises GFP.

7. The method of claim 1, wherein the fluorescent protein comprises the amino acid sequence of SEQ ID NO: 9 or SEQ ID NO: 10.

8. The method of claim 1, wherein the first polynucleotide and the second polynucleotide are expressed as a fusion protein.

9. The method of claim 1, further comprising exposing the *E. coli* cells to a test compound added to the first liquid culture.

10. The method of claim 9, wherein the test compound is a mutagen.

* * * * *